(12) United States Patent
Hawrot

(10) Patent No.: US 6,753,315 B2
(45) Date of Patent: Jun. 22, 2004

(54) α-BUNGAROTOXIN MOLECULES AND USES THEREOF

(75) Inventor: Edward Hawrot, Barrington, RI (US)

(73) Assignee: Brown University Research Foundation, Providence, RI (US)

( * ) Notice: Subject to any disclaimer, the term of this patent is extended or adjusted under 35 U.S.C. 154(b) by 82 days.

(21) Appl. No.: 09/819,058

(22) Filed: Feb. 23, 2001

(65) Prior Publication Data

US 2002/0081291 A1 Jun. 27, 2002

Related U.S. Application Data

(60) Provisional application No. 60/184,518, filed on Feb. 24, 2000.

(51) Int. Cl.$^7$ .......................... A61K 38/00; A01N 37/18
(52) U.S. Cl. ....................................................... 514/12
(58) Field of Search ........................ 424/239.1; 514/1, 514/411, 2, 12

(56) References Cited

U.S. PATENT DOCUMENTS

| | | | |
|---|---|---|---|
| 5,053,005 A | | 10/1991 | Borodic |
| 5,171,750 A | * | 12/1992 | Brossi et al. ............... 292/340 |
| 5,298,019 A | | 3/1994 | Borodic |
| 5,401,243 A | * | 3/1995 | Borodic ....................... 128/898 |
| 5,562,907 A | | 10/1996 | Arnon |
| 5,677,308 A | | 10/1997 | Lerner |
| 5,714,468 A | | 2/1998 | Binder |
| 5,721,215 A | | 2/1998 | Aoki et al. |
| 5,766,605 A | * | 6/1998 | Sanders et al. ............. 128/898 |
| 5,869,068 A | * | 2/1999 | De Lacharriere et al. ... 424/401 |

OTHER PUBLICATIONS

Garcia–Borron JC, Bieber AL, Martinez–Carrion M. Reductive methylation as a tool for the identification of the amino groups in alpha–bungarotoxin interacting with nicotinic acetylcholine receptor. Biochemistry. Jul. 1987 14;26(14):4295–303.*
Lin SR, Chang CC. Studies on the status of amino groups in alpha–bungarotoxin. Toxicon. 1991;219(8):937–50. (Abstract).*
Sargent, Annu. Rev. Neurosci. 16:403–443, 1993.
McGehee & Role, Annu. Rev. Physiol. 57:521–546, 1995.
Boyd, Crit. Rev. Toxicol. 27:299–318, 1997.
Dani & Heinemann, Neuron 16: 905–908, 1996.
Endo & Tamiya, in Snake Toxins A.L. Harvey, Ed.:165–222, Pergamon Press, Inc., NY 1991.
Chiappinelli, Natural and Synthetic Neurotoxins, A. Harvey, ed.: 65–128, Acad. Press, NY 1995.
Changeux et al., Proc. Natl.Acad. Sci. USA 67: 1241–1247, 1970.
Whiting & Lindstrom, Biochem. 25:2082–2093, 1986.
Whiting & Lindstrom, Proc. Natl. Acad. Sci. USA 84:595–599, 1987.
Chiappinelli et al., Toxicon 34:1243–1256, 1996.
Grant et al., Biochem. 37:12166–12171, 1998.
Cartier et al., J. Biol. Chem.271:7522–7528, 1996.
Luo et al., J. Neurosci. 18:8571–8579, 1998.
GenBank accession No. X91990.
GenBank accession Nos. AF056400–AF056417.
GenBank accession No. AJ131356.
GenBank accession No. Y17057.
GenBank accession No. Y17058.
GenBank accession No. Y17693.
GenBank accession No. Y17694.
Bushara, Med. Hypotheses 48(4):337–339, 1997.
Pal et al., Neurology 54(1):244–247, 2000.
Koman et al., J. Pediatr. Orthop. 20(1):108–115, 2000.
Kolbasnik et al., Am. J. Gastroenterol. 94(12):3434–3439, 1999.
Wehrmann et al., Gastrointest. Endosc. 50(4):545–548, 1999.
Dawson et al., Ophthalmology 106(9):1727–1730, 1999.
Carruthers et al., J. Am. Acad. Dermatol. 34(5 Pt 1):788–797, 1996.
Frankel et al., Arch. Otolaryngol. Head Neck Surg. 124(3):321–323, 1998.
Carruthers et al., Dermatol. Surg. 24(11):1244–7, 1998.
Bertrand et al., Meth. Neurosci. 4:174–193, 1991.
Levandoski et al. J. Biol. Chem. 274:26113–26119, 1999.
Mebs et al. Hoppe–Seyler's Z. Physiol. Chem. 353:243–262, 1972.
Fiordalisi & Grant, Toxicon 31:767–775, 1993.
Rosenthal, Ph.D. Thesis, Brown University, 1996.
Rosenthal et al., J. Biol. Chem. 269:11178–11185, 1994.
Rosenthal et al., Biochem. 38:7847–7855, 1999.
Riemann et al., Ophthalmology 106(12):2322–2324, 1999.
Orloff et al., Otolaryngol. Head Neck Surg. 121(4):410–413, 1999.
Pillet et al., J. Biol. Chem. 268:909–916, 1993.
Fiordalisi et al., Biochem. 33:3872–3877, 1994.
Zeng et al., J. Biol. Chem. 276:22930–22940, 2001.
Spura et al, J. Biol. Chem. 275:22452–22460, 2000.
Levandoski et al., J. Neurochem. 74:1279–1289, 2000.
Spura et al., Biochem. 38:4912–4921, 1999.
Pestronk and Drachman, J. Neurosci. 5(3):751–758, 1985.

* cited by examiner

Primary Examiner—Karen Cochrane Carlson
Assistant Examiner—Sheridan Snedden
(74) Attorney, Agent, or Firm—Wolf, Greenfield & Sacks, P.C.

(57) ABSTRACT

This invention relates to compositions and methods for the specific inhibition of neurotransmission. More specifically, the invention relates to isolated modified α-bungarotoxin molecules that show high specificity for nicotinic acetylcholine receptors. Such modified α-bungarotoxin molecules, as well as native α-bungarotoxin molecules, are useful in a variety of conditions where localized inhibition of neuronal and/or muscle cell function is desirable.

14 Claims, 11 Drawing Sheets

FIG. 6

α-BUNGAROTOXIN MOLECULES AND USES THEREOF

RELATED APPLICATIONS

This application claims priority under 35 U.S.C. §119 from U.S. provisional application Ser. No. 60/184,518, filed Feb. 24, 2000. +gi

Government Support

This work was funded in part by the National Institutes of Health under grant number NIH-R01-NS34348. The government may retain certain rights in this invention.

FIELD OF THE INVENTION

This invention relates to modified α-bungarotoxin molecules and to methods for selectively inhibiting neurotransmitter receptors using modified and unmodified α-bungarotoxin molecules. More specifically, the invention relates to the use of α-bungarotoxin compositions for the localized inhibition of neuronal and/or muscle cell function.

BACKGROUND OF THE INVENTION

At the neuromuscular junction, the nicotinic acetyicholine receptor (nAChR) mediates muscle contraction through the binding at the muscle membrane surface of acetyicholine, which is released from the skeletal motorneuron. There is growing evidence that nAChRs in the nervous system play critical roles in a wide variety of physiological responses and pathological states (Sargent, *Annu. Rev. Neurosci.* 16:403–443, 1993; McGehee & Role, *Annu. Rev. Physiol.* 57:521–546, 1995; Boyd, *Crit. Rev. Toxicol.* 27:299–318, 1997), and mediate the behavioral effects of nicotine (Dani & Ileinemann, *Neuron* 16:905–908, 1996). The class of snake venom proteins known as a-neurotoxins, which are competitive antagonists of nAChRs, have been extremely useful tools in the study of the al-subunit containing muscle-type nAChR and the α7-subunit containing neuronal nAChR (Endo & Tamiya, in *Snake Toxins* A.L. Harvey, Ed., pp 165–222, Pergamon Press, Inc., New York, N.Y., 1991; Chiappinelli, in *Natural and Synthetic Neurotoxins*, A. Harvey, ed., pp.65–128, Academic Press, New York, N.Y., 1995). α-Neurotoxins have a highly conserved fold, due primarily to four invariant disulfide bonds and are classified as either "short" with 60–62 residues and four disulfides, or "long" with 66–74 residues and a fifth disulfide. The long α-neurotoxin, α-bungarotoxin (αBgtx), from the venom of *Bungarus multicinctus,* has played a critical role in the biochemical purification and characterization of nAChRs from muscle (e.g., Changeux et al., *Proc. Natl.Acad Sci. USA* 67:1241–1247, 1970) and brain (Whiting & Lindstrom, *Biochem.* 25:2082–2093, 1986; Whiting & Lindstrom, *Proc. Nati. Acad Sci. USA* 84:595-599, 1987) due to the essentially irreversible binding of aBgtx to these receptors.

Venom-derived αBgtx has been a critically important tool in biochemical studies of nAChRs largely because of its high affinity and nearly irreversible binding characteristics (Chiappinelli, 1995). Similar biochemical studies of most neuronal nAChRs, apart from α7 subunit-containing receptors, have been hampered by the lack of similar high-affinity probes. κ-Bungarotoxin blocks cholinergic transmission in peripheral nervous tissue (e.g., Chiappinelli et al., *Toxicon* 34:1243–1256, 1996) and has a high specificity for α3β2 receptors (Grant et al., *Biochem.* 37:12166–12171, 1998), but this toxin is in relatively short supply. Recently, two naturally-occurring toxins isolated from the venom of Conus snails have been shown to be selective for α3β2 and α3β4 nAChRs (Cartier et al., *J. Biol. Chem.* 271:7522–7528, 1996; Luo et al., *J. Neurosci.* 18:8571–8579, 1998) although their utility may be limited by their very rapid dissociation kinetics. Thus there is a need for additional well characterized molecular probes of high specificity for investigation of the properties of nAChRs, particularly α7 subunit-containing nAChRs.

Bacterial, snake and snail toxins typically affect neurotransmitter uptake and/or release at neuromuscular synapses. Despite their lethality, a variety of these toxins are used as therapeutic agents in human disease. For example, treatment of certain neuromuscular disorders involving local muscle spasticity or dystonia (see, e.g., U.S. Pat. Nos. 5,721,215; 5,677,308; 5,562,907, 5,053,005, etc.) involves injection of a chemodenervating agent, currently a botulinum toxin preparation (BOTOX®, Allergan, Irvine, Calif.), directly into the muscle, using, for example, a fine gauge teflon-coated needle under electromyographic control to aid the physician in locating the intended intramuscular locus of the injection. A sufficient dose of the toxin acts on striated muscle to block release of the acetylcholine neurotransmitter from the presynaptic membrane resulting in varying degrees of effective denervation of the muscle in regions contacted by the toxin (i.e., causing local paralysis). This results in an increase in post-synaptic acetylcholinesterase activity and an increase in the population of acetylcholine receptors, effects which occur as a characteristic physiological response to denervation. After a period of days, the axon terminals develop sprouting, and over a period of several months, collateral motor axons establish new neuromuscular connections with the muscle fiber. As neuromuscular junctions are regenerated, full function of the muscle returns along with the spasmodic contractions or hyperstimulation symptomatic of the disease.

Botulinum toxin treatment is also known to be associated with a number of side effects. Such side effects include transient fatigue, dysphagia, neck weakness, hoarseness and localized pain. In addition, many patients who preliminarily respond to botulinum toxin therapy subsequently become non-responsive to the treatment. Accordingly, for many patients the botulinum injections fail to provide satisfactory long term treatment of the condition. Thus there is a need to develop additional chemodenervating agents that do not have the foregoing deficiencies of botulinum toxin.

SUMMARY OF THE INVENTION

The invention provides compositions and methods for nonpermanent and localized inhibition of neuronal cell function. It has now been discovered that α-bungarotoxin and modified α-bungarotoxin molecules are useful for reducing neurotransmitter effects at neuromuscular junctions, thereby inducing the temporary paralysis of muscles. These effects are useful for the treatment of aberrant muscle contraction, inter alia in the cosmetic treatment of facial wrinkles, in strabismus, blepharospasm, various dystonias and other conditions having neuromuscular components.

According to one aspect of the invention, methods of enhancing relaxation or slackening of cutaneous tissue are provided. The methods include locally administering to a cutaneous tissue an isolated native or modified α-bungarotoxin molecule in an amount effective to enhance denervation of the muscle or group of muscles present subcutaneous to the cutaneous tissue to enhance relaxation or slackening of the cutaneous tissue. In some embodiments, the α-bungarotoxin is administered subcutaneously.

Preferably the relaxation or slackening of the cutaneous tissue results in lessening of wrinkles or fine lines of the skin. In some embodiments the methods further include co-administering an anti-wrinkle agent selected from the group consisting of hydroxy acids and retinoids. In preferred embodiments the hydroxy acid is selected from the group consisting of α-hydroxy acids and β-hydroxy acids, which can be linear, branched or cyclic and saturated or unsaturated and the retinoid is selected from the group consisting of retinoic acid, retinol and retinol esters.

In certain embodiments, the α-bungarotoxin molecule is an isolated native α-bungarotoxin molecule or a fragment thereof, preferably one that includes SEQ ID NO:2. On other embodiments, the α-bungarotoxin molecule is an isolated modified α-bungarotoxin molecule or a fragment thereof. Preferred modified α-bungarotoxin molecules include those having at least one amino acid substitution selected from the group consisting of a substitution at amino acid 38 and a substitution at amino acid 42 of SEQ ID NO:2.

According to another aspect of the invention, methods of treating spasm or involuntary contraction in a muscle or a group of muscles in a subject are provided. The methods include administering to a muscle or a group of muscles in a subject in need of such treatment an isolated native or modified α-bungarotoxin molecule, in an amount effective to inhibit spasm or involuntary contraction in the muscle or the group of muscles of the subject.

In some embodiments the subject in need of such treatment has blepharospasm, strabismus, spasmodic torticollis, focal dystonia, jaw dystonia, occupational dystonia, corneal ulceration (protective ptosis), spasmodic dysphonia (laryngeal dystonia), or facial dyskinesis such as Meige syndrome, hemifacial spasm, aberrant regeneration of facial nerves, or apraxia of eyelid opening.

In certain embodiments, the α-bungarotoxin molecule is an isolated native α-bungarotoxin molecule or a fragment thereof, preferably one that includes SEQ ID NO:2. On other embodiments, the α-bungarotoxin molecule is an isolated modified α-bungarotoxin molecule or a fragment thereof. Preferred modified α-bungarotoxin molecules include those having at least one amino acid substitution selected from the group consisting of a substitution at amino acid 38 and a substitution at amino acid 42 of SEQ ID NO:2.

According to yet another aspect of the invention, methods of controlling autonomic nerve function in a subject are provided. The methods include locally administering to a target tissue or organ of a subject in need of such treatment an isolated native or modified α-bungarotoxin, in an amount effective to enhance denervation in the target tissue or organ and control autonomic nerve function in the subject.

In some embodiments, the autonomic nerve function includes the function of an autonomic nerve which contributes to at least one symptom of rhinorrhea, otitis media, excessive salivation, asthma, chronic obstructive pulmonary disease, excessive stomach acid secretion, spastic colitis or excessive sweating.

In certain embodiments, the α-bungarotoxin molecule is an isolated native α-bungarotoxin molecule or a fragment thereof, preferably one that includes SEQ ID NO:2. On other embodiments, the α-bungarotoxin molecule is an isolated modified α-bungarotoxin molecule or a fragment thereof. Preferred modified α-bungarotoxin molecules include those having at least one amino acid substitution selected from the group consisting of a substitution at amino acid 38 and a substitution at amino acid 42 of SEQ ID NO:2.

According to still another aspect of the invention, isolated polypeptide which selectively bind nicotinic acetylcholine receptors with a non-native specificity are provided. The polypeptides include the amino acid sequence of SEQ ID NO:2 having at least one amino acid substitution, or a fragment thereof.

In certain embodiments the at least one amino acid substitution is selected from the group consisting of a substitution at amino acid 38 and a substitution at amino acid 42 of SEQ ID NO:2. Preferably the at least one amino acid substitution is selected from the group consisting of Pro at amino acid 38 and Gln at amino acid 42 of SEQ ID NO:2. More preferably, the isolated polypeptide includes the amino acid sequence of SEQ ID NO:2 having amino acid substitutions of Pro at amino acid 38 and Gln at amino acid 42.

Pharmaceutical compositions, including the foregoing isolated polypeptides and a pharmaceutically acceptable carrier, also are provided according to the invention. Preferably a pharmaceutically effective amount of the isolated polypeptides is included in the pharmaceutical composition.

According to another aspect of the invention, pharmaceutical composition are provided that include an isolated native α-bungarotoxin and a pharmaceutically acceptable carrier.

These and other aspects of the invention, as well as various advantages and utilities, will be more apparent with reference to the detailed description of the preferred embodiments.

BRIEF DESCRIPTION OF THE DRAWINGS

FIG. 6. Circular Dichroism Spectrum of rBgtx.

DETAILED DESCRIPTION OF THE INVENTION

Figure 1A:
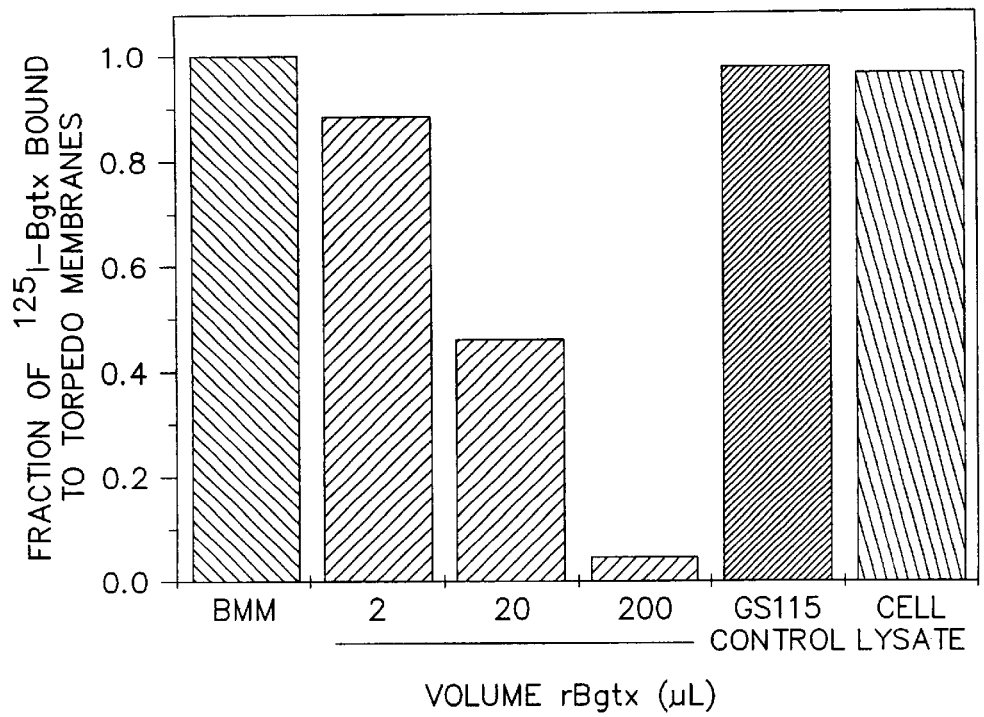
FIG. 1. A. Competition Binding of rBgtx Induced Cultures. B. Time Course of rBgtx Accumulation Upon Induction.

It has now been discovered that α-bungarotoxin (in both isolated native and modified forms) is useful in the treatment of a variety of conditions characterized by aberrant muscle activity. α-Bungarotoxin molecules can be used for the treatment of disorders in the manner of botulinum toxin A. Furthermore, the invention includes the identification of modified α-bungarotoxin molecules that have altered binding specificities. In particular, modification of residues 38 (Lys) and 42 (Leu) to Pro and Gln, respectively, altered the binding specificity of α-bungarotoxin from α7-containing nicotinic acetylcholine receptors to α3β2-containing nicotinic acetylcholine receptors. Additional modifications to these amino acid residues and other amino acid residues are possible.

Thus the invention embraces functional variants of α-bungarotoxin. As used herein, a "functional variant," "variant" or "modification" of an α-bungarotoxin molecule (i.e., a "modified α-bungarotoxin") is a molecule which contains one or more modifications to the primary amino acid sequence (including inter-amino acid bonds) of known native α-bungarotoxin molecules and retains the nAchR receptor-binding properties disclosed herein (e.g., binding to α7- or α3β2 nAchRs). As used herein, "native" α-bungarotoxin molecules are those found in the venom of *Bungarus multicinctus*. The complete amino acid sequence of native α-bungarotoxin molecules and the DNA sequences that encode them have been published (see, e.g., GenBank accession numbers X91990, AF056400-AF056417, AJ131356, Y17057, Y17058, Y17693, Y17694). Accordingly, a DNA clone encoding a native α-bungarotoxin can be obtained by one of ordinary skill in the art, using published sequence information, and conventional recombinant DNA techniques.

Modifications which create an α-bungarotoxin functional variant can be made for example 1) to enhance a property of an α-bungarotoxin, such as polypeptide stability in an expression system or the stability of protein-protein binding such as α-bungarotoxin-nAchR binding; 2) to provide a novel activity or property to an α-bungarotoxin molecule, such as addition of a detectable moiety; or 3) to provide a different amino acid sequence that produces the same or similar receptor binding properties. Modifications to an α-bungarotoxin molecule can be made to a nucleic acid which encodes the peptide, and can include deletions, point mutations, truncations, amino acid substitutions and additions of amino acids. Alternatively, modifications can be made directly to the polypeptide, such as by cleavage, addition of a linker molecule, addition of a detectable moiety, such as biotin, addition of a fatty acid, substitution of one amino acid for another and the like. Modifications also embrace fusion proteins comprising all or part of the α-bungarotoxin amino acid sequences disclosed herein.

Functional variants of native and modified α-bungarotoxin molecules include fragments of the polypeptide molecules. A fragment, as used herein, is an α-bungarotoxin molecule lacking one or more amino acids of a native α-bungarotoxin amino acid sequence. Fragments may have amino acid(s) removed from one or both ends of the α-bungarotoxin molecule, or in the internal sequence of the molecule, and combinations of these. The fragments retain at least a portion of the nAchR binding activity of the complete α-bungarotoxin molecule from which the fragments were derived (native of modified α-bungarotoxin molecules). It is within the skill of one of ordinary skill in the art to test the fragments to determine the binding activity of the fragment. Exemplary methods for determining nAchR binding are provided below in the Examples.

If a functional variant of the α-bungarotoxin molecules include an amino acid substitution without a change in binding specificity, then conservative amino acid substitutions typically will be preferred, i.e., substitutions which retain a property of the original amino acid such as charge, hydrophobicity, conformation, etc. Examples of conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

The invention also includes the use of nucleic acid sequences which include alternative codons that encode the same amino acid residues of the α-bungarotoxin molecules. Leucine residues, for example, can be encoded by the codons CUA, CUC, CUG, CUU, UUA and UUG. Each of the six codons is equivalent for the purposes of encoding a leucine residue. Thus, it will be apparent to one of ordinary skill in the art that any of the leucine-encoding nucleotide triplets may be employed to direct the protein synthesis apparatus, in vitro or in vivo, to incorporate a leucine residue. Similarly, nucleotide sequence triplets which encode other amino acid residues include: GUA, GUC, GUG and GUU (valine codons); GGU, GGA, GGG, GGC (glycine codons); UAC and UAU (tyrosine codons). Other amino acid residues may be encoded similarly by multiple nucleotide sequences. Thus, the invention embraces degenerate nucleic acids that differ from the nucleic acids encoding native α-bungarotoxin molecules in codon sequence due to the degeneracy of the genetic code.

The invention also provides modified nucleic acid molecules which include additions, substitutions and deletions of one or more nucleotides. In preferred embodiments, these modified nucleic acid molecules and/or the polypeptides they encode retain at least one activity or function of the unmodified nucleic acid molecule and/or the polypeptides, such as receptor binding. In certain embodiments, the modified nucleic acid molecules encode modified polypeptides, preferably polypeptides having conservative amino acid substitutions as are described elsewhere herein. The modified nucleic acid molecules are structurally related to the unmodified nucleic acid molecules and in preferred embodiments are sufficiently structurally related to the unmodified nucleic acid molecules so that the modified and unmodified nucleic acid molecules hybridize under stringent conditions known to one of skill in the art, such as those described in *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York.

For example, modified nucleic acid molecules which encode polypeptides having single amino acid changes can be prepared (e.g., residues critical for nAchR binding). Each of these nucleic acid molecules can have one, two or three nucleotide substitutions exclusive of nucleotide changes corresponding to the degeneracy of the genetic code as described herein. Likewise, modified nucleic acid molecules which encode polypeptides having two amino acid changes can be prepared which have, e.g., 2–6 nucleotide changes. Numerous modified nucleic acid molecules like these will be readily envisioned by one of skill in the art, including for example, substitutions of nucleotides in codons encoding amino acids 2 and 3, 2 and 4, 2 and 5, 2 and 6, and so on. In the foregoing example, each combination of two amino acids is included in the set of modified nucleic acid molecules, as well as all nucleotide substitutions which code for the amino acid substitutions. Additional nucleic acid molecules that encode polypeptides having additional substitutions (i.e., 3 or more), additions or deletions (e.g., by introduction of a stop codon or a splice site(s)) also can be prepared and are embraced by the invention as readily envisioned by one of ordinary skill in the art. Any of the foregoing nucleic acids or polypeptides can be tested by routine experimentation for retention of structural relation or activity to the nucleic acids and/or polypeptides disclosed herein.

It will also be understood that the invention embraces the use of the sequences in expression vectors, as well as to transfect host cells and cell lines, be these prokaryotic (e.g., *E. coli*), or eukaryotic (e.g., yeast expression systems, CHO cells, COS cells, and recombinant baculovirus expression in insect cells). The expression vectors require that the pertinent sequence, i.e., those described supra, be operably linked to a promoter.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids, phagemids, bacteria genomes and virus genomes. A cloning vector is one which is able to replicate in a host cell or be replicated after its integration into the genome of a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Preferably, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA) encoding an α-bungarotoxin molecule. That heterologous DNA (RNA) is placed under operable control of transcriptional elements to permit the expression of the heterologous DNA in the host cell.

Preferred systems for mRNA expression in mammalian cells are those such as pcDNA3.1 (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences.

The expression vector is selected to be compatible with the host organism. A wide variety of host/expression vector combinations can be employed for expressing the α-bungarotoxin molecule encoding DNA. Numerous host cell lines, expression vectors, and expression vector components are commercially available. Compatible host/expression vector combinations can be readily selected by those of skill in the art. In a preferred embodiment of the invention, the host organism is *Pichea pastoris* and the expression vector is one of the pPIC series vectors (Invitrogen; Carlsbad, Calif.; see also Examples section).

The preferred method for obtaining the α-bungarotoxin molecules for use in this invention is by recombinant production, which involves genetic transformation of a host cell with a recombinant DNA vector encoding the α-bungarotoxin molecules, expression of the recombinant DNA in the transformed host cell, and collection and purification of the α-bungarotoxin. Preferably, the host organism is unicellular. More preferably, the host organism is a yeast, particularly *Pichea pastoris.*

Isolated α-bungarotoxin molecules are preferred in all embodiments of the invention. As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. An isolated nucleic acid as used herein is not a naturally occurring chromosome.

As used herein with respect to polypeptides, "isolated" means separated from its native environment and present in sufficient quantity to permit its identification or use. Isolated, when referring to a protein or polypeptide, means, for example: (i) selectively produced by expression cloning or (ii) purified as by chromatography or electrophoresis. Isolated proteins or polypeptides may, but need not be, substantially pure. The term "substantially pure" means that the proteins or polypeptides are essentially free of other substances with which they may be found in nature or in vivo systems to an extent practical and appropriate for their intended use. Substantially pure polypeptides may be produced by techniques well known in the art. Because an isolated protein may be admixed with a pharmaceutically acceptable carrier in a pharmaceutical preparation, the protein may comprise only a small percentage by weight of the preparation. The protein is nonetheless isolated in that it has been separated from the substances with which it may be associated in living systems, i.e. isolated from other proteins.

The invention also embraces methods of treatment for conditions where temporary muscle paralysis is desirable. A number of such conditions call for such treatment, and are similar to those disease states where botulinum toxin administration is currently being utilized. Examples of such disease states and methods of administration are described in detail in U.S. Pat. Nos.: 5,298,019 to Borodic (decreasing spasm or involuntary contraction in a muscle or group of muscles of a patient induced by pathologic neural stimulation caused by cerebrospinal injury or stroke); 5,721,215 to Aoki et al. (treatment of neuromuscular disorders); 5,766,605 to Sanders et al. (controlling autonomic nerve function); 5,714,468 to Binder (reduction of migraine headache pain); 5,670,484 to Binder (treating skin lesions associated with a cutaneous cell-proliferative disorder); 5,766,605 to Sanders et al. (to control the function of an autonomic nerve which contributes to at least one symptom of rhinorrhea, otitis media, excessive salivation, asthma, chronic obstructive pulmonary disease, excessive stomach acid secretion, spastic colitis or excessive sweating); and other patents in the patent families of the foregoing, the contents of which are expressly incorporated herein by reference in their entirety.

Injection of the parotid glands with the α-bungarotoxin molecules disclosed herein also is useful in the treatment of sialorrhea in patients with amyotrophic lateral sclerosis, Parkinson's disease and other neurological diseases (Bushara, *Med. Hypotheses* 48(4):337–339, 1997; Pal et al., *Neurology* 54(1):244–247, 2000). The α-bungarotoxin molecules also can be used for treatment of cerebral palsy-related lower extremity spasticity (Koman et al., *J. Pediatr. Orthop.* 20(1):108–115, 2000), achalasia (Kolbasnik et al., *Am. J. Gastroenterol.* 94(12):3434–3439, 1999), pathologic lacrimation (Riemann et al., *Ophthalmology* 106(12):2322–2324, 1999), vocal fold granulomas (Orloff et al., *Otolaryngol. Head Neck Surg.* 121(4):410–413, 1999), pancreas divisum and acute recurrent pancreatitis, (Wehrmann et al., *Gastrointest. Endosc.* 50(4):545–548, 1999), acute-onset esotropia (Dawson et al., *Ophthalmology* 106(9):1727–1730, 1999), and other conditions, especially those which benefit from amelioration of aberrant muscle control.

The α-bungarotoxin molecules also can be used for cosmetic treatments, including alone (Carruthers et al., *J. Am. Acad. Dermatol.* 34(5 Pt 1):788–977, 1996; Frankel et al., *Arch. Otolaryngol Head Neck Surg.* 124(3):321–323, 1998), in combination with other anti-wrinkle agents useful in cosmetic skin treatment, or in combined therapy with laser resurfacing and surgical procedure (Carruthers et al., *Dermatol. Surg.* 24(11):1244–7, 1998), and the like. As is known to one of ordinary skill in the art, anti-wrinkle agents include α-hydroxy acids and β-hydroxy acids, which can be linear, branched or cyclic and saturated or unsaturated, retinoids including retinoic acid, retinol and retinol esters, and the agent described in U.S. Pat. No. 5,869,068.

The α-bungarotoxin molecules that selectively bind to α3β2 nAchR molecules (e.g., the rBgtx-K38P/L42Q molecule) and interfere with dopamine-mediated neurotransmission will also be useful in the treatment of various disorders. These include, but are not limited to, treatment of psychoses (see, e.g., U.S. Pat. No. 5,922,679), treatment of nicotine dependence (see, e.g., U.S. Pat. No. 5,780,433), and treatment of mood disorders (see, e.g., U.S. Pat. No. 5,929,034).

Methods of treatment according to the present invention comprise the administration of α-bungarotoxin molecules to effectively and temporarily block synaptic transmission in the manner of botulinum toxin treatment.

The α-bungarotoxin molecules of the invention are administered in effective amounts. An effective amount is a dosage of the α-bungarotoxin molecule sufficient to provide a medically desirable result. The effective amount will vary with the particular condition being treated, the age and physical condition of the subject being treated, the severity of the condition, the duration of the treatment, the nature of the concurrent therapy (if any), the specific route of administration and like factors within the knowledge and expertise of the health practitioner. For example, in connection with treating spasm or involuntary contraction in a muscle or a group of muscles in a subject, an effective amount is that amount which inhibits or reduces the spasm or involuntary contraction. Likewise, an effective amount for lessening the appearance of wrinkles or fine lines in the skin would be an amount sufficient to lessen or inhibit the muscular contractile tone of the group of muscles present subcutaneously under the wrinkled cutaneous surface so as to allow relaxation of the cutaneous surface and enhance its smoothness. Thus, it will be understood that the α-bungarotoxin molecules of the invention can be used to treat the above-noted conditions according to the preferred modes of administration described below. It is preferred generally that a maximum dose be used, that is, the highest safe dose according to sound medical judgment. Repeated administrations of small doses so as to reduce 'spillage' and therefore unnecessary toxicity in the non-affected, non-targeted tissue/neurons are also preferred.

A subject, as used herein, refers to any mammal (preferably a human, and including a non-human primate, cow, horse, pig, sheep, goat, dog, cat or rodent) with a condition requiring inhibition of neuronal activity, leading to extended periods of denervation and/or paralysis (such as the conditions described above).

An α-bungarotoxin molecule of the invention may be administered alone or as part of a pharmaceutical composition. Such a pharmaceutical composition may include the α-bungarotoxin molecule in combination with any standard physiologically and/or pharmaceutically acceptable carriers which are known in the art. The compositions should be sterile and contain a therapeutically effective amount of the α-bungarotoxin molecule in a unit of weight or volume suitable for administration to a patient. The term "pharmaceutically-acceptable carrier" as used herein means one or more compatible solid or liquid filler, diluents or encapsulating substances which are suitable for administration into a human or other animal. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy. Pharmaceutically acceptable further means a non-toxic material, that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

Compositions suitable for parenteral administration conveniently comprise sterile aqueous and non-aqueous preparations of the α-bungarotoxin molecules of the invention. This aqueous preparation may be formulated according to known methods using suitable dispersing or wetting agents and suspending agents. Aqueous carriers include water, alcoholic/aqueous solutions, emulsions or suspensions, including saline and buffered media. Examples of non-aqueous solvents are propylene glycol, polyethylene glycol, vegetable oils such as olive oil, and injectable organic esters such as ethyl oleate, and including synthetic mono- or di-glycerides. The sterile injectable preparation also may be a sterile injectable solution or suspension in a non-toxic parenterally-acceptable diluent or solvent, for example, as a solution in 1,3-butane diol. In addition, fatty acids such as oleic acid may be used in the preparation of injectables. Preferred parenteral vehicles include sodium chloride solution, Ringer's dextrose, dextrose and sodium chloride, lactated Ringer's or fixed oils. Carrier formulations suitable for subcutaneous, intravenous, intramuscular, etc. administrations can be found in Remington's Pharmaceutical Sciences, Mack Publishing Co., Easton, Pa. Preservatives and other additives may also be present such as, for example, antimicrobials, anti-oxidants, chelating agents, and inert gases and the like.

A variety of administration routes are available. The particular mode selected will depend, of course, upon the particular drug selected, the severity of the condition being treated, and the dosage required for therapeutic efficacy. The methods of the invention, generally speaking, may be practiced using any mode of administration that is medically acceptable, meaning any mode that produces effective levels of the active compounds without causing clinically unacceptable adverse effects. Typically such modes of administration include parenteral routes. The term "parenteral" includes subcutaneous, intramuscular, intradermal or topical infusion. Intramuscular routes are preferred. Oral and intravenous administration should be avoided due to the toxicity associated with the agents of the invention.

The pharmaceutical compositions may conveniently be presented in unit dosage form and may be prepared by any of the methods well-known in the art of pharmacy. All methods include the step of bringing the α-bungarotoxin molecules of the invention into association with a carrier which constitutes one or more accessory ingredients. In general, the compositions are prepared by uniformly and intimately bringing the α-bungarotoxin molecules into association with a liquid carrier, a finely divided solid carrier, or both, and then, if necessary, shaping the product.

Other delivery systems can include time-release, delayed release or sustained release delivery systems. Such systems can avoid repeated administrations of the α-bungarotoxin molecules of the invention, increasing convenience to the subject and the physician. Many types of release delivery systems are available and known to those of ordinary skill in the art. They include the above-described polymeric systems, as well as polymer base systems such as poly (lactide-glycolide), copolyoxalates, polycaprolactones, polyesteramides, polyorthoesters, polyhydroxybutyric acid, and polyanhydrides. Microcapsilles of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the α-bungarotoxin molecule is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be particularly suitable for treatment chronic conditions. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

The α-bungarotoxin molecules of the invention may be administered alone or in combination (co-administered) with the above-described drug therapies by any conventional route, including injection, repeated injection, topical application, etc., over time. The administration may, for example, be intraperitoneal, intramuscular, intra-cavity, subcutaneous, or transdermal. When using the α-bungarotoxin molecules of the invention, direct administration to the affected site (e.g., muscles with involuntary spasm, wrinkle, etc.) such as administration by injection, is preferred.

The term "co-administered," means administered substantially simultaneously with another agent. By substantially simultaneously, it is meant that an α-bungarotoxin molecule is administered to the subject close enough in time with the administration of the other agent (e.g., an anti-wrinkling agent, etc.). The other agent may be present in a different formulation than the α-bungarotoxin molecule, or it may be part of the same formulation.

The co-administered agent can act cooperatively, additively or synergistically with an α-bungarotoxin molecule to produce a desired effect, for example, lessening of wrinkles. The other agent is administered in effective amounts. Such amounts maybe less than these sufficient to provide a therapeutic benefit when the agent is administered alone and not in combination with an α-bungarotoxin molecule of the invention. A person of ordinary skill in the art would be able to determine the effective amounts needed.

The invention will be more fully understood by reference to the following examples. These examples, however, are merely intended to illustrate the embodiments of the invention and are not to be construed to limit the scope of the invention.

EXAMPLES

We describe a system for the recombinant expression and purification of native and modified α-bungarotoxin (αBgtx) molecules from the methylotropic yeast *Pichia pastoris*. We have previously reported the expression of αBgtx as a fusion protein in *E. coli* (Rosenthal et al., 1994, 1999). We have now developed a recombinant αBgtx Pichia system to circumvent two major difficulties of the *E. coli* system, namely, the requirements of an in vitro proteolysis reaction to liberate the αBgtx from its fusion partner and of a refolding procedure to generate the five proper disulfide bonds of αBgtx. We demonstrate that the Pichia-expressed, purified recombinant αBgtx has activity identical to venom-derived αBgtx, and that this expression system facilitates the protein engineering of αBgtx. We show that a double point mutant of αBgtx, rBgtx-K38P/L42Q, unlike wild type αBgtx, blocks acetylcholine-evoked currents mediated by α3β2 neuronal nAChRs heterologously expressed in Xenopus oocytes. This demonstration of altered specificity for receptors represents an increase in the affinity of αBgtx for α3β2 receptors of several orders of magnitude.

Experimental Methods

Chemicals and Reagents. All chemicals (Sigma; St. Louis, Mo.) were reagent grade except for HPLC grade water and acetonitrile used in HPLC applications. For cloning work, enzymes and reagents (Gibco-BRL, Gathersburg, Md.) were molecular biology grade. Venom-derived Bgtx (αBgtx) was from Research Biochemicals, Inc. (Natick, Mass.), $^{125}$I-Bgtx was from New England Nuclear (Boston, Mass.). Yeast media were composed of the following: YPD-1% yeast nitrogen base, $4\times10^{-5}$ M biotin, 1% glycerol, pH 5.8; BMM-identical to BMG except for the replacement of glycerol with 2% methanol.

Construction of αBgtx Expression Vectors. A synthetic gene coding for αBgtx, SEQ ID NO:1, composed of codons preferentially used in *P. pastoris* as are well known in the art (see, e.g., various internet-based compilations of codon usage such as http://www.kazusa.orjp/codon/ or text compilations such as *Molecular Biology LABFAX, I: Recombinant DNA,* T. A. Brown, ed. Academic Press, 1998), was made using an overlapping oligonucleotide strategy and subcloned into the pPIC9 (using SnaBI and NotI), pPIC9K (using BamHI and NotI) and pPICZαA (using XhoI and NotI) vectors (Invitrogen; Carlsbad, Calif.). These vectors bear the pre-pro sequence of the *S. cerevisae* alpha mating factor, which directs secretion of gene products fused to it; the rBgtx is liberated from this peptide by endogenous specific endopeptidases during maturation. Point mutants of rBgtx were created with the PCR-based QuikChange technique (Stratagene; La Jolla, Calif.) with Pfu polymerase. Sequences were confirmed either by the manual dideoxy technique using Sequenase 2.0 (United States Biochemicals; Cleveland, Ohio.) or by a PCR-based fluorescent dye method at the Brown University Sequencing Facility. The predicted amino acid sequence of the αBgtx gene constructs is identical to that of the venom-derived toxin, (IVCHTTATSPISAVTCPPGENLCYRKMWCDAFCSSR-GKVVELGCAATCPSKKPYEEVTCCSTDKCNPHPKQ-RPG, SEQ ID NO:2) with the exception of the addition of an N-terminal Tyr. This residue addition is a consequence of the cloning strategy used, which involved insertion into a restriction site in the appropriate vector. The limited availability of suitable restriction sequences dictated the necessity of incorporating a N-terminal Tyr residue downstream of but in frame with the alpha mating factor signal sequence and signal cleavage site. αBgtx gene constructs, under the control of the methanol-inducible AOX1 promoter, were stably integrated into the methanol utilization positive (Mut$^+$) GS115 strain by homologous recombination. All manipulations of yeast strains and initial screening for protein expression were done following protocols recommended by Invitrogen or practiced routinely in the field (Higgins & Cregg, eds. *Methods in Molecular Biology* Vol. 103, *Pichea Protocols,* Humana Press, Totowa, N.J., 1998).

Expression and Purification of Recombinant αBgtx. GS115/rBgtx cultures induced in BMM for 3–4 days were cleared of cells by centrifugation at 3400× g for 5 min. The toxin-containing spent medium was then passed through 0.2 μm filters to remove large particulates, and the filtered sample was concentrated by ultrafiltration with a 1000 MW cutoff (YM1) membrane in a 2-L stirred cell (Amicon; Bedford, Mass.). Following dialysis against 50 mM ammonium acetate, pH 5.0, the concentrated crude medium fraction was applied to a CM-Sephadex C-25 (Pharmacia; Piscataway, N.J.) weak cation exchange resin equilibrated in 50 mM ammonium acetate, pH 5.0. A linear gradient from the equilibration buffer to 1 M ammonium acetate, pH 6.0, was used to elute the rBgtx. The rBgtx-containing fraction was then desalted and further purified by HPLC on a Vydac C18 (The Separations Group; Hesperia, Calif.) reverse phase column using a linear gradient of 0–60% (1% per minute; flow rate 1 mL/min) acetonitrile in water plus 0.1% trifluoroacetic acid (TFA). A final step of cation exchange chromatography on a PolyCat A (Poly LC; Columbia, Md.) HPLC column was done with a linear gradient from the equilibration buffer of 50 mM ammonium acetate, pH 6.0, 40% acetonitrile, to 300 mM ammonium acetate, pH 6.0, 40% acetonitrile (1% per minute; flow rate 1 mL/min). For analysis, samples were desalted using pre-packed PD10columns (Pharmacia) following the manufacture's protocol, or using C18 reverse phase HPLC.

Protein Analysis. Recombinant αBgtx proteins were characterized with a number of physical techniques. Sodium dodecyl sulfate polyacrylamide gel electrophoresis (SDS-PAGE) using 16.5% gels in a tricine buffer system was carried out as described by Schager and von Jagow (1987). The molecular mass of the purified rBgtx was determined by electrospray mass spectrometry (Dr. Paul Barlow, University of Edinburgh). Amino-terminal amino acid sequencing was carried out at the Keck Biotechnology Resource Laboratory at Yale University. Circular dichroism spectra were measured in an OLIS CD spectrophotometer with ~12 μM rBgtx or venom-derived αBgtx in water. Protein concentrations were routinely measured with at least two of the following methods: measuring absorbance at 275 nm with an empirically-determined extinction coefficient for venom-derived αBgtx of $1.01\times10^4$ $M^{-1}cm^{-1}$; using a BCA colorimetric assay (Pierce; Rockford, Ill.) with venom-derived αBgtx as standards; integrating the area of the two peaks (cf. FIG. 3B) eluting at 33–35 minutes from a C18 reverse phase column and comparing to standards of authentic αBgtx of known mass applied to the column.

Electrophysiological Recordings with Xenopus Oocytes. Measurements of acetylcholine-evoked currents from Xenopus oocytes expressing defined combinations of nAChR subunit genes by the two electrode voltage-clamp method were performed as described by Bertrand et al. (*Meth. Neurosci.* 4:174–193, 1991) and Levandoski et al. (*J. Biol. Chem.* 274:26113–26119, 1999). All work with Xenopus was approved by Brown University Institutional Animal Care and Use Committee. The neuronal nAChR subunit genes in the pGEM-HE background were the gift of Charles Leutje; the 5HT$_3$ receptor clone was provided by David Julius. A ten-minute incubation with toxin solution, while the oocyte was still impaled in the recording chamber, was used to avoid excessive manipulation of oocytes. The time is sufficient to achieve maximal block of muscle-type nAChRs with concentrations of toxin greater than ~10 nM (Levandoski et al., 1999). Fractional block of evoked currents was determined as the ratio of peak current recorded after toxin exposure compared to the peak current recorded prior to the addition of toxin.

Torpedo nAChR Competition Binding Assay. Competition with $^{125}$I-Bgtx binding to Tropedo nAChR-enriched membranes was measured as previously described (Rosenthal et al., 1994, 1999). Briefly, the membrane preparation was plated by centrifugation at a constant concentration (~3 nM toxin binding sites) in the wells of a microtiter plate (Nunc MaxiSorb, Nalgene). Mixtures of a constant concentration of $^{125}$I-Bgtx (8 nM) and varying concentrations of unlabeled competitor in 10 mM sodium phosphate, 0.2% bovine serum albumin, pH 7.4, were added to duplicate wells in a final volume of 0.1 mL and allowed to incubate at room temperature for 2 hours. After removal of unadsorbed material by aspiration and washing, the radioactivity remaining in the wells was determined. Plots Of $^{125}$I-Bgtx remaining bound in the presence of competitor as a function of the competitor concentration were fit to the logistic equation (Limbird, 1996) using Origin software (Microcal, Northampton, Mass.).

Expression of αBgtx from Pichia pastoris. In order to circumvent the very inefficient and laborious refolding steps required when a αBgtx is expressed as a fusion protein in E. coli (Rosenthal et al., 1994, 1999), we decided to express αBgtx in the yeast Pichia pastoris. Recombinant expression in this yeast takes advantage of its secretory capability. As αBgtx is normally secreted into venom glands, we reasoned that the post-translational processing and protein folding might be similar in this simple eukaryote. A synthetic αBgtx gene was prepared using an overlapping oligonucleotide strategy. This product was designed to have SnaBI and NotI restriction endonuclease sites flanking the amino- and carboxyl-termini of the sequence, respectively. Utilizing these sites in the pPIC9 vector, the αBgtx gene was subcloned in frame with the pre-pro leader sequence of the S. cerevisiae alpha mating factor, which normally directs the secretion of this protein pheromone. The transformation vector also contained the HIS4 locus, and thus stable integration of the αBgtx gene construct into the GS115 background strain (auxotrophic for histidine) could be selected by plating cells on medium lacking hisitidine.

After screening a large number of GS115/rBgtx tranformants (>50) in small cultures (Higgins & Cregg, 1998) for the presence of rBgtx protein using SDS-PAGE analysis, we demonstrated that significant αBgtx activity could be produced in larger cultures ($\leqq$100 mL). Following 2–4 days of induction in 2% methanol/BMM medium, the cell-free medium was tested directly for competition with $^{125}$I-labeled venom-derived αBgtx for binding to Torpedo nAChR-enriched membranes as described under Experimental Methods. Increasing volumes of spent GS115/rBgtx medium, following five days of induction of BMM medium, were incubated with 8 nM $^{125}$I-Bgtx and ~3 nM nAChR sites in a final volume of 220 μL. The decrease in radioactivity bound was dose-dependent. In contrast, 200 μL of the BMM medium alone, 200 μL of an induced culture of the background strain GS 115, or the soluble fraction of the lysate of induced GS 115/rBgtx cells equivalent to 200 μL of culture did not compete for toxin binding. The ~45% reduction in $^{125}$I-Bgtx bound for the 20 μL aliquot of GS115/rBgtx corresponds to ~5 ng of αBgtx, based on calibration using a titration of venom-derived αBgtx in the same assay (cf. FIG. 5), or about 250 μg/L total.

FIG. 1A shows that the reduction in $^{125}$I-Bgtx bound to Torpedo membranes was dependent on the volume of spent medium assayed. BMM medium in which no culture was grown, untransformed GS115 cultures induced in the same manner as GS115/rBgtx cultures, and the soluble fraction of induced GS115/rBgtx cell lysate all failed to compete for toxin binding.

Figure 1B:
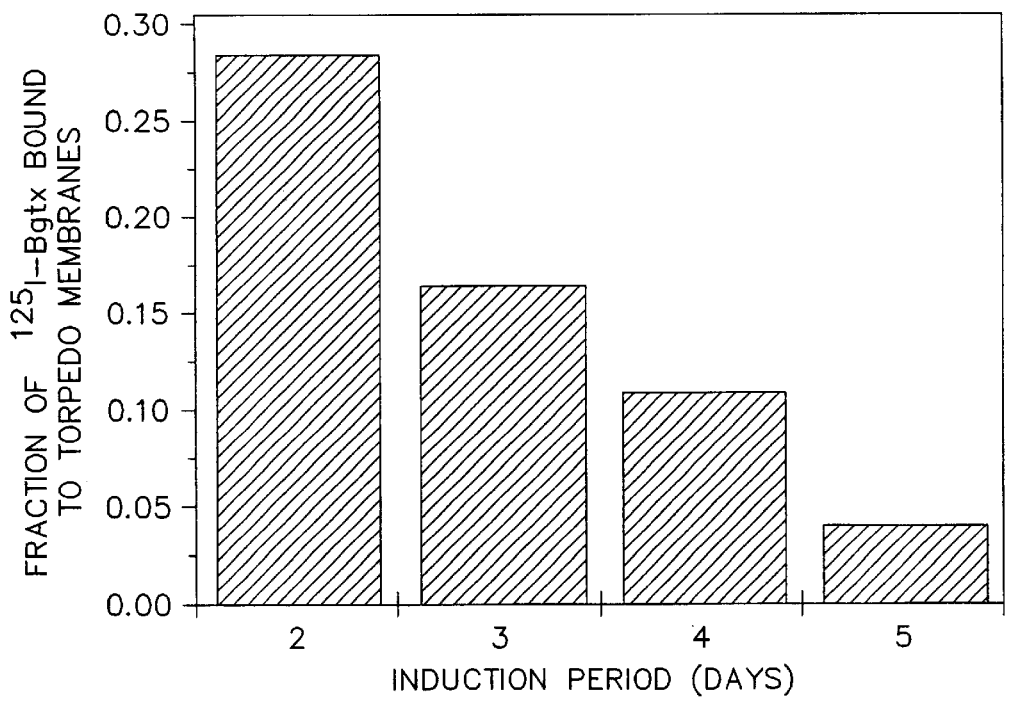

The increase in αBgtx binding activity present in 200 μL aliquots of spent GS115/rBgtx cultures following induction in BMM was monitored as a function of time. The data point at five days in this panel corresponds to the 200 μL point in panel A. All data in this figure, normalized to radioactivity bound in the absence of competitor, are averages of duplicate measures (relative error ±3%) and are representative of three or more experiments. As shown in FIG. 1B, the αBgtx activity present in spent culture medium increased over the course of five days. In addition, spent culture medium obtained from induced GS115/rBgtx cultures contained a protein that migrated on SDS-polyacrylamide gels near the position of venom-derived αBgtx (e.g., see below, FIG. 4).

To optimize the expression of rBgtx, we drew extensively on examples from the literature (for review, see Higgins & Cregg, 1998). Initial trials of expression using large volumes in shaker flasks yielded about 1 mg/L (0.13 μM) of αBgtx activity as measured by competition binding calibrated with standards of venom-derived αBgtx. Pichia expression of αBgtx was initially tested by generating a Pichia-expression construct by PCR using another αBgtx expression vector (Rosenthal et al., 1994) which contained codons preferentially used in E. coli. To test whether codons preferentially utilized in P. pastoris would improve expression, the vectors described in the Methods section above were constructed. Switching to the Pichia codons resulted in no significant increase in expression levels.

With many other recombinant proteins, multiple gene copies give rise to enhanced expression levels (Higgins & Cregg, 1998). Therefore, the corresponding pPIC9K-Bgtx and pPICZαA-Bgtx vectors were prepared; these are intended, by virtue of drug resistance genes borne on the plasmids, to facilitate identification of transformants which have undergone multiple insertion events. Strains resistant to high concentrations of drug (e.g., 2.0 mg/mL G418 in the case of the pPIC9K-Bgtx vector or 2.0 mg/mL Zeocin for pPICZαA-Bgtx) do not appear to produce any more αBgtx activity than the original GS115/rBgtx strains. Also, no further increase in αBgtx expression was observed for transformants of KM71, a strain which utilizes methanol slowly, or SMD1168H, a protease-deficient strain.

Modest two- to four-fold variations in rBgtx expression levels could be achieved by altering the media components and growth conditions. Expression was induced with 0.5, 1.0 and 2.0% methanol/BMM; supplementing the induction medium with yeast extract and peptone, casamino acids or cysteine; cultures were induced at various points of the growth phase and at various cell densities. In addition, high-density fermentation was performed in a 2-L Virtis benchtop fermentor. α-Bungarotoxin was expressed from a GS115/rBgtx strain by an initial growth phase in BMG for about 24 hours, until a density of $OD_{600}$~1–2 was reached. The BMG medium was then replaced with BMM containing 2% methanol and grown for another 4 days at 30° C. with daily additions of 2% methanol. This procedure yielded the equivalent of ~2 mg of αBgtx activity per liter (i.e., 0.25 μM) of cell-free medium as measured by competition binding.

Figure 2A:
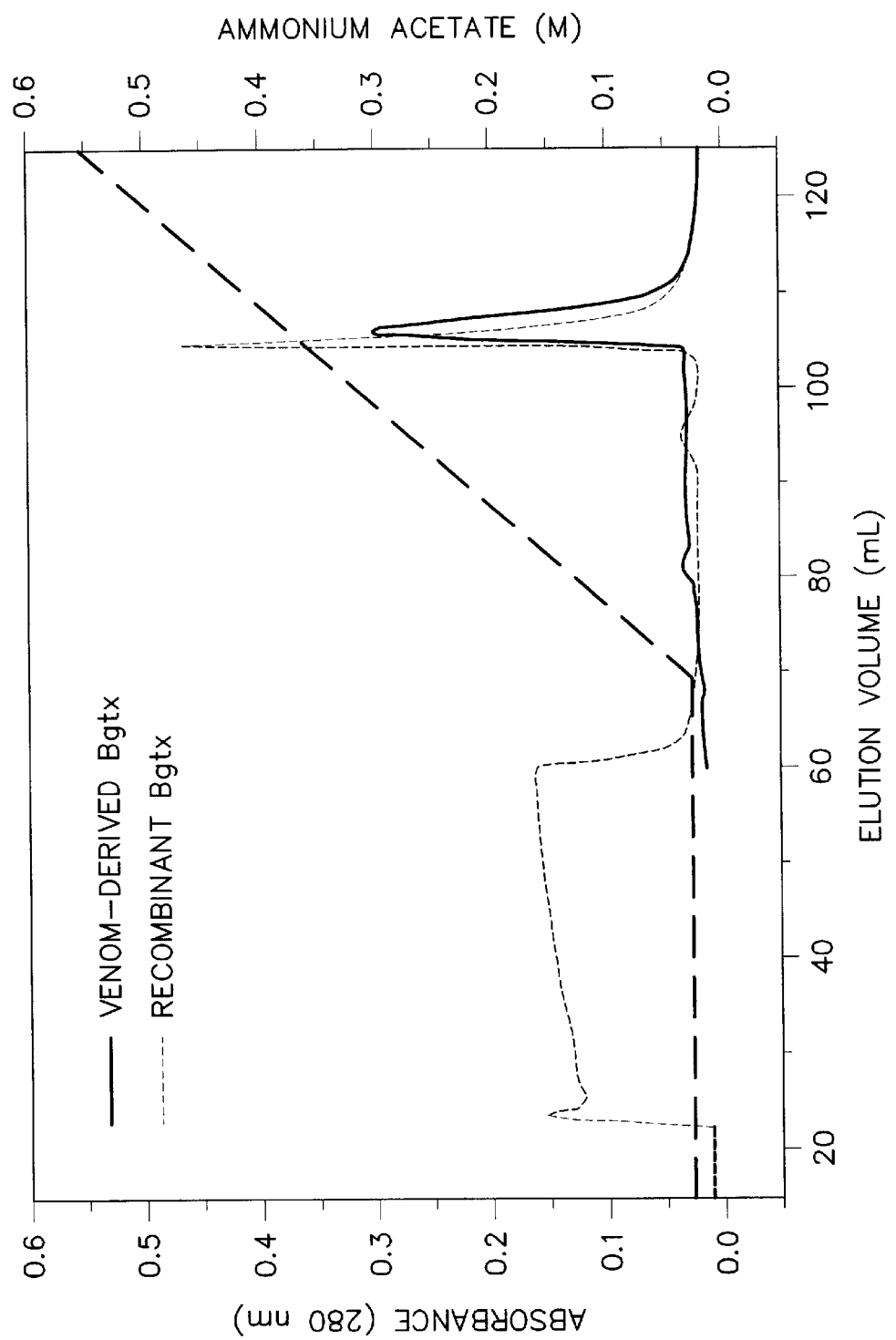
FIG. 2. A. Cation Exchange Chromatography of rBgtx. B. Reverse Phase HPLC Chromatography of Enriched rBgtx.

Purification of Recombinant αBgtx. After large scale cultures expression rBgtx were cleared of yeast by centrifugation and filtration, spent medium was concentrated 20–40-fold using a pressurized ultrafiltration device and a 1000 MW cutoff membrane. Samples were then dialyzed against 50 mM ammonium acetate, pH 5.0 for cation exchange (CM-Sephadex C-25) chromatography. The chromatograms (FIG. 2A) of a sample of recombinant αBgtx (dotted trace) and a standard of venom-derived αBgtx (solid trace) were obtained by monitoring absorbance at 280 nm as a function of elution volume. The sample of recombinant αBgtx, concentrated 20-fold and dialyzed against 50 mM ammonium acetate, pH 5.0, was applied to a 20 mL (bed volume) column of CM-Sephadex C-25 equilibrated in the same buffer. After the sample was loaded and all unadsorbed material washed through (approx. 65 mL), a linear gradient from 50 mM ammonium acetate, pH 5.0, to 1.0 M ammonium acetate, pH 6.0, was applied to the column (indicated by the dashed line). The recombinant and venom-derived toxins eluted at 0.3–0.4 M ammonium acetate. The two traces were aligned at the point at which the gradient was started due to the fact that the pure venom-derived αBgtx standard had no component that washed through the column. This is consistent with the results of Mebs et al. (*Hoppe-Seyler's Z. Physiol. Chem.* 353:243–262, 1972) who purified αBgtx from *B. multicinctus* venom using a similar procedure.

Figure 2B:
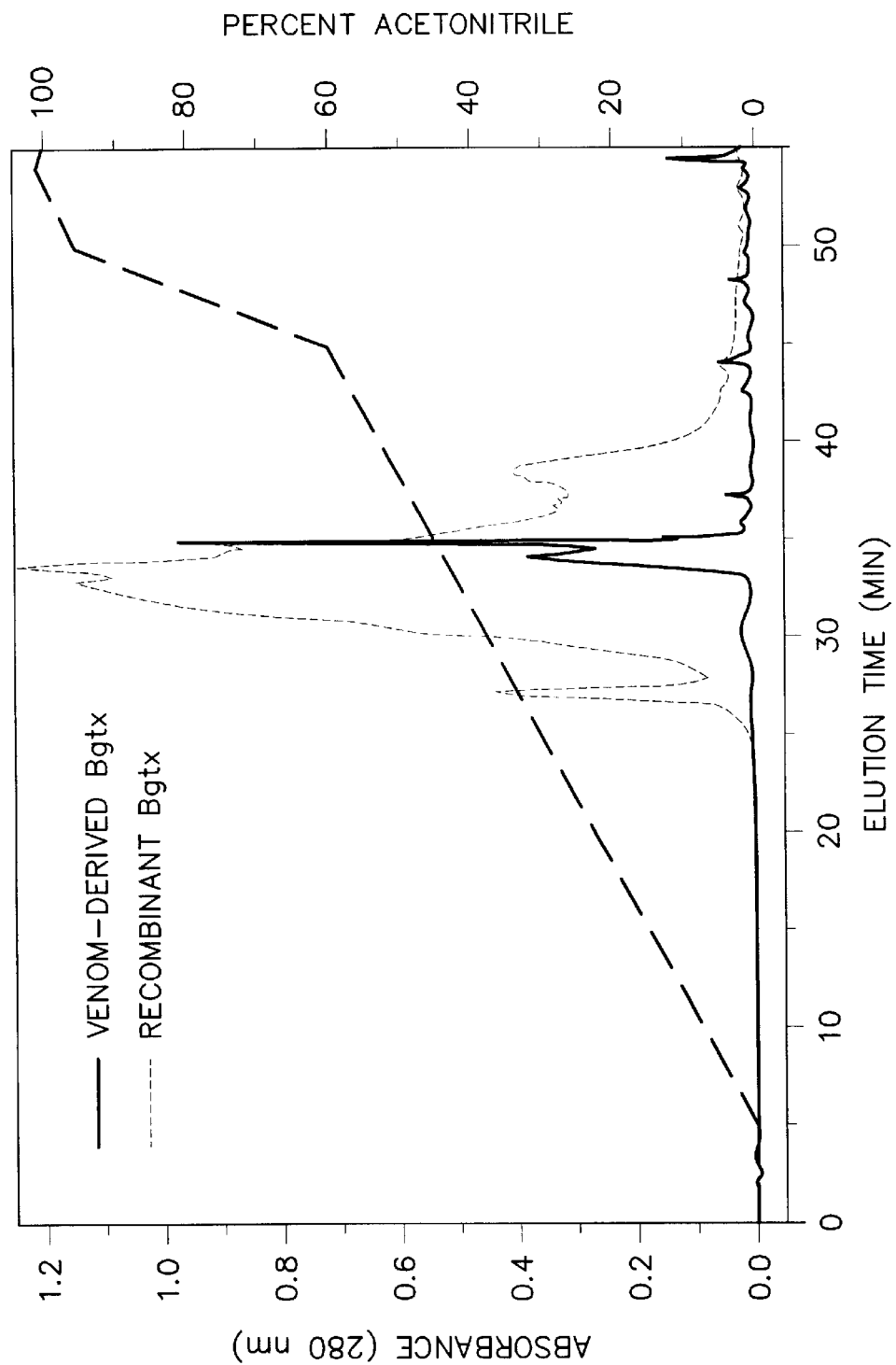

Upon C18 reverse phase HPLC, the peak material taken from the cation exchange column eluted as a broad range of peaks from about 30–55% acetonitrile (FIG. 2B). The rBgtx fraction eluting as a single peak from CM-Sephadex resin (105–115 mL in FIG. 2A) was applied to a Vydac C18 reverse column equilibrated with 0.1% TFA in water. A linear gradient of 0.1% TFA to 60% acetonitrile, 0.1% TFA over 40 minutes (dashed lines) was then applied to the column and the absorbance at 280 nm was monitored. The rBgtx material eluted (dotted trace) over a wide range (25–40 minutes) as a complex, incompletely resolved series of peaks. In contrast, a standard sample of venom-derived αBgtx applied to the C18 column (solid trace) using the same protocol eluted as two sharp, well-resolved peaks at 33–35 minutes.

This result is in contrast to purified venom-derived toxin, which elutes at 33–35 minutes (about 40% acetonitrile) as two sharp peaks. These two peaks are chemically identical and apparently represent different conformers of αBgtx (Fiordalisi & Grant, *Toxicon* 31:767–775, 1993; Rosenthal et al., 1994). Competition binding analysis and SDS-PAGE revealed that the recombinant activity co-eluted with venom-derived αBgtx. The material that eluted from the C18 column at lower acetonitrile concentrations had a higher apparent molecular weight (~12 kDa) than authentic αBgtx and is a glycosylated form of the toxin (see below).

Figure 3A:
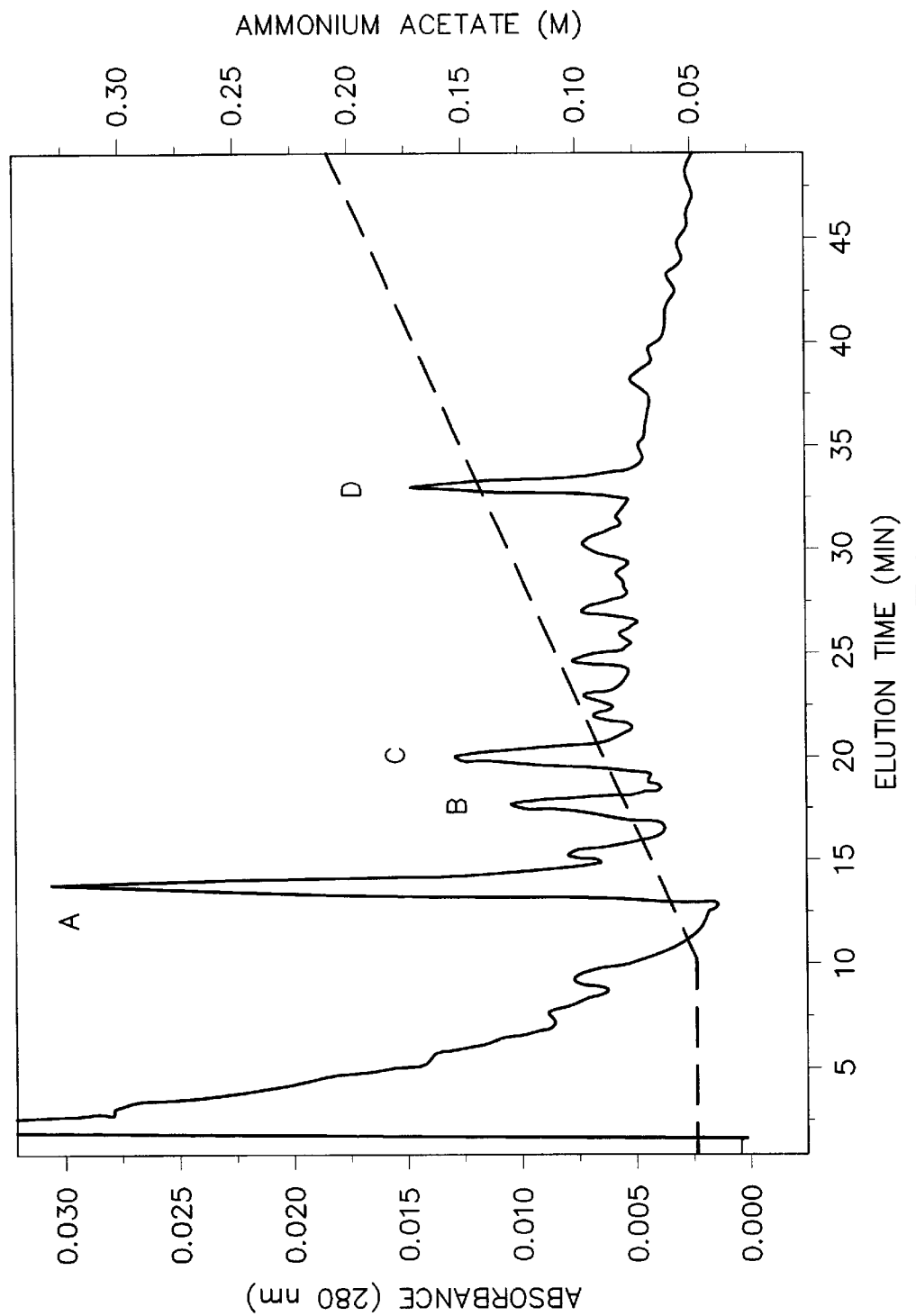
FIG. 3. A. HPLC-Based Cation Exchange of rBgtx. B. Analytical Reverse Phase HPLC of rBgtx Purified by Poly-Cat A Chromatography.

The active rBgtx fractions were then applied to an HPLC weak cation exchange column. The portion of rBgtx fraction eluting between 33 and 40 minutes from C18 reverse phase chromatography (FIG. 2B) was applied to a PolyCat A column equilibrated in 50 mM ammonium acetate, pH 6.0, 40% acetonitrile. After washing though unadsorbed material for 10 minutes, proteins were eluted with a linear gradient (dashed line) of 50–300 mM ammonium acetate, pH 6.0, 40% acetonitrile over 60 minutes. FIG. 3A shows that the linear gradient resolved the sample into a series of discrete peaks. Several distinct fractions were collected (labeled A-D); the binding activity in competition assays and the mobility in SDS-PAGE relative to venom-derived αBgtx were determined for each fraction.

Figure 3B:
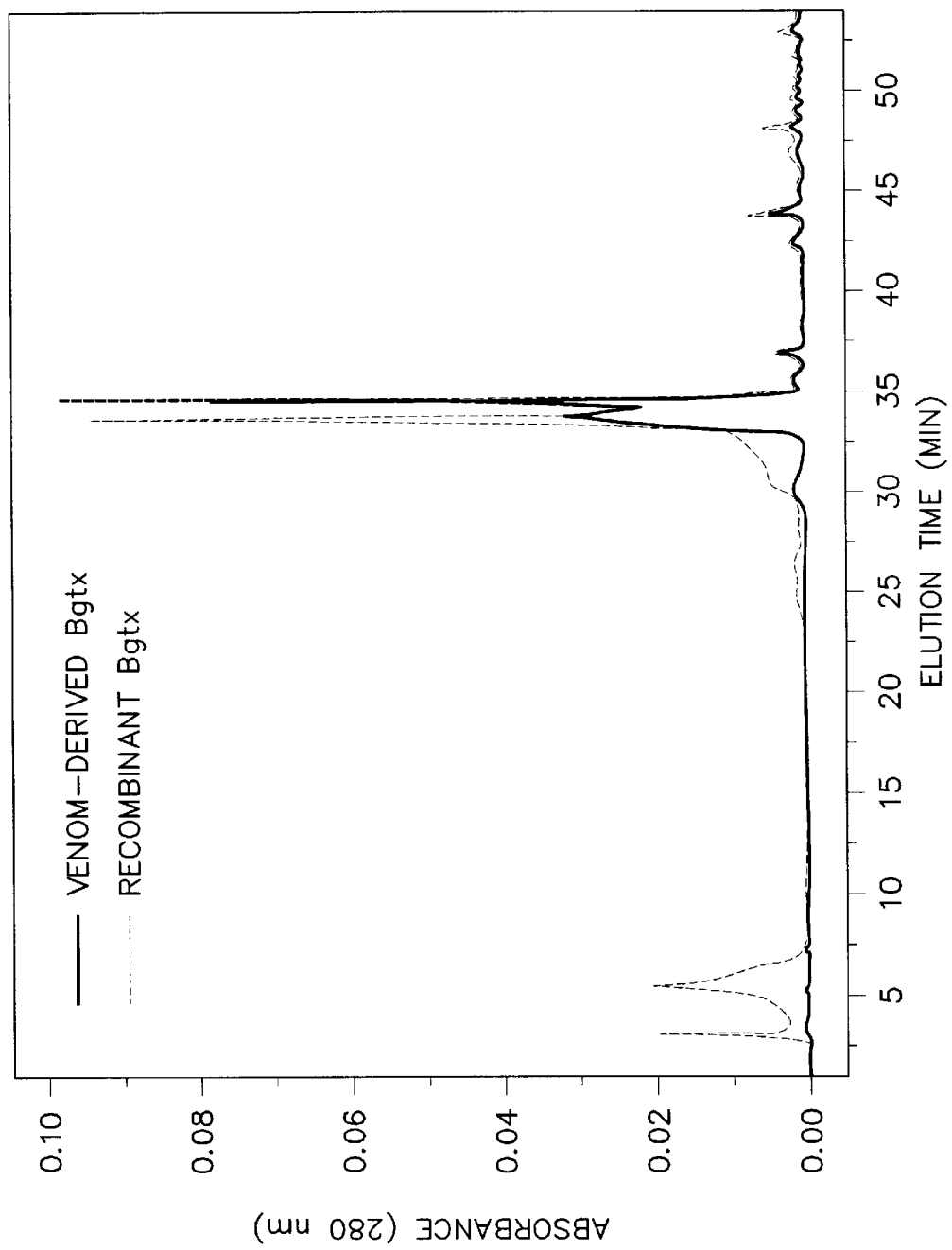

It was found that "peak C" contained recombinant αBgtx with the properties of authentic αBgtx. This is demonstrated in FIGS. 4–6. First, the material of "peak C" from PolyCat A cation exchange HPLC was re-applied to an analytical C18 reverse phase column (FIG. 3B). The dotted trace shows the elution from a C18 column of the protein that eluted between 19 and 21 minutes from the PolyCat A column ("peak C" in FIG. 3A). The chromatographic parameters were the same as described for FIG. 2B. For comparison, the solid trace shows the elution profile of venom-derive αBgtx. The rBgtx material was characterized by an elution time very similar to that of venom-derived αBgtx. In addition, it displayed the two interconvertible peaks characteristic of the conformational equilibrium seen with authentic αBgtx (Fiordalisi & Grant, 1993). The difference in relative intensities of the two peaks in the recombinant sample as compared to authentic Bgtx could be due to equilibrium perturbations induced by the additional N-terminal acids retained in the rBgtx (see below).

A Coomassie-stained polyacrylamide gel verified the purity of "peak C" material (i.e., single protein band in lanes 10 and 12 of FIG. 4A), and also revealed that the apparent mobility of the rBgtx was significantly retarded relative to venom-derived αBgtx. Samples of rBgtx from various stages of expression and purification were analyzed on a 16.5% SDS-polyacrylamide gel using a tricine buffer system. Lane 1 shows a set of standards, with their apparent molecular masses indicated to the left. In lanes 2, 9, 11 were loaded with 5 μg of venom-derived αBgtx. The arrow indicates the 8 kDa apparent molecular mass of the venom-derived toxin. The samples in lanes 3–8 represent 0.5 mL aliquots of the cell-free medium taken at 0–5 days after induction of a GS115/rBgtx culture in BMM medium. The upper, less intense band of the two evident upon induction contains an apparently glycosylated form of rBgtx. Lane 10 represents about 0.5 μg of the "peak C" fraction from PolyCat A chromatography (see FIG. 3) and lane 12 was loaded with 5 μg of purified recombinant αBgtx obtained following analytical reverse phase chromatography (FIG. 3B). The slightly retarded mobility of the rBgtx samples with respect to that of venom-derived αBgtx is due to an amino terminal addition of five residues. The samples in lanes 1–8 and those of lanes 9–12 were run on two separate gels.

To confirm the apparent discrepancy in the apparent mobility of the rBgtx, amino-terminal sequencing and mass spectrometry was carried out on various fractions. Two N-terminal sequences, YIVCH (SEQ ID NO:3) and EAEAYIVCH (SEQ ID NO:4), could be detected in samples of intermediate purity (i.e., through C18 reverse phase HPLC but not fractionated further by PolyCat A cation exchange HPLC) but the relative amounts of the two forms could not be readily quantitated. The first sequence represents complete cleavage by the endogenous protease KEX2 and STE13 of Pichia, whereas the second sequence indicates cleavage by only KEX2. A similar retention of the secretion signal sequence-derived EAEA (SEQ ID NO:5) sequence has been observed in other recombinant proteins expressed with this same Pichia secretion system (e.g., Hawrot et al., *FEBS Lett.* 432:103–108, 1998). The N-terminal sequence information therefore verified that the protein fraction isolated through that stage of purification contains Bgtx. It also suggested that the higher apparent molecular weight of the more highly purified rBgtx analyzed in FIG. 4A was due to the presence of the additional N-terminal EAEA (SEQ ID NO:5) sequence.

Figure 4A:
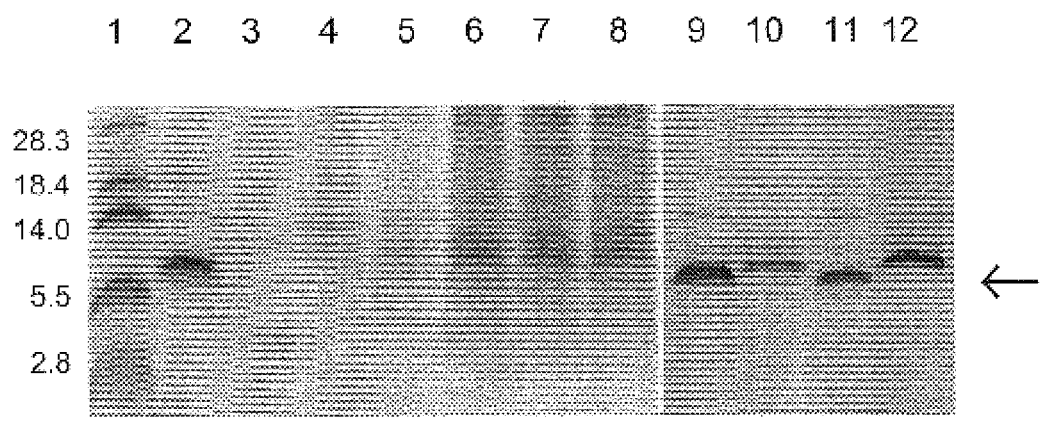
FIG. 4. A. SDS-Gel Analysis of rBgtx Fractions. B. Mass Spectrometric Analysis of rBgtx.
Figure 4B:
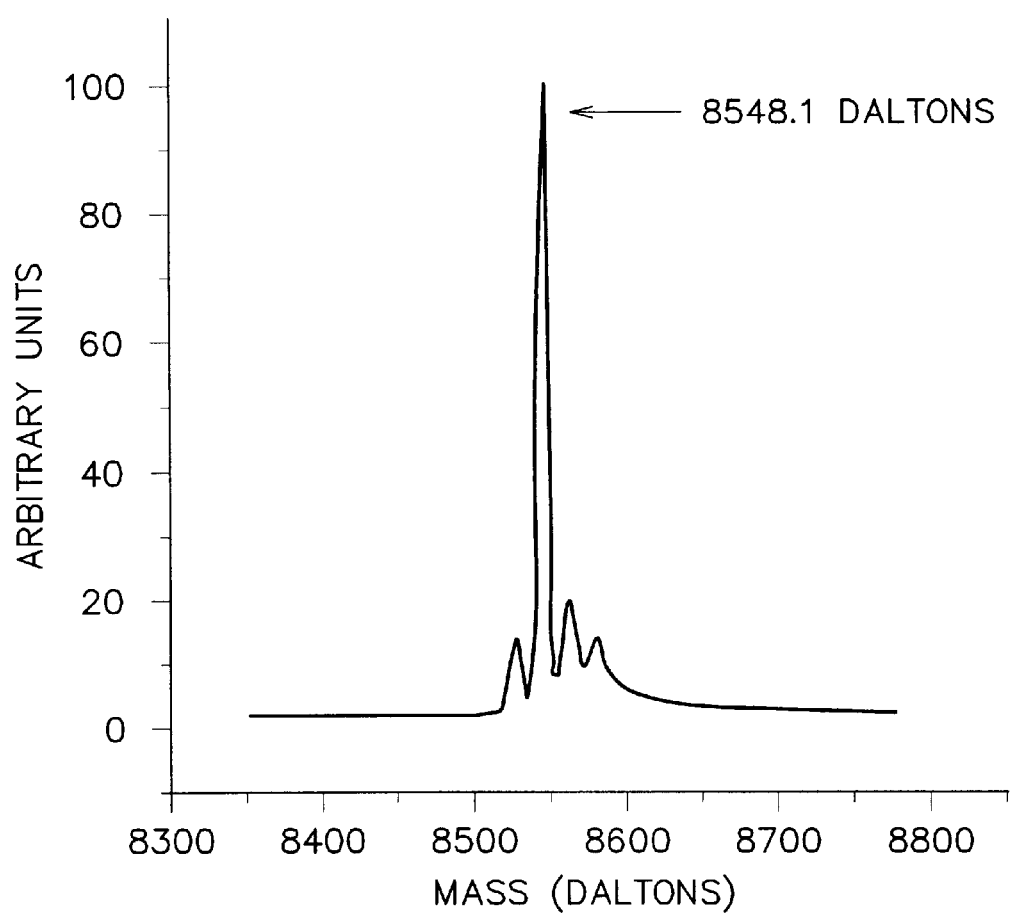

Mass spectrometric analysis was used to test this by characterizing the mass of the material purified through the PolyCat A cation exchange HPLC step of purification (i.e., fractions analyzed in lanes 10 and 12 of FIG. 4A). Approximately 2.5 μg of purified rBgtx (sample identical to that illustrated above in lane 12 of FIG. 4A with a purity of >95%) was analyzed by electrospray mass spectrometry. As shown in FIG. 4B, the deconvoluted spectrum revealed a major peak with a mass of 8548.1 daltons. Several other analyses of rBgtx samples isolated from different preparations gave similar results. This value compared very well with the theoretical mass of 8547.8 predicted for the N-terminal addition of EAEAY (SEQ ID NO:6) onto the Bgtx amino acid sequence. Theoretical molecular weights were calculated from the primary amino acid sequence using the programs available on the http://expasy.ch proteomics server. As a reference, purified, venom-derived Bgtx gave a mass of 7985.0 daltons as compared to its theoretical mass of 7984.3 daltons (data not shown). These observations suggest that the purified rBgtx contains the N-terminal extension, EAEAY (SEQ ID NO:6), attached to the primary sequence of authentic Bgtx.

Further analysis of other fractions isolated after PolyCat A cation exchange HPLC failed to reveal a significant amount of rBgtx with the minimal addition of an N-terminal Tyr (i.e., lacking the EAEA (SEQ ID NO:5) extension). No abundant fraction could be identified which contained a protein band that co-migrated exactly with venom-derived Bgtx. We believe that the rBgtx molecules with the Tyr minimal addition may either represent an extremely small fraction of that rBgtx which lacks carbohydrate modification or that they may be associated with the major portion of rBgtx that is secreted in a glycosylated form.

The ability of purified rBgtx ("peak C" fraction from PolyCat A chromatography) to compete with $^{125}$I-labeled venom-derived αBgtx for binding to Torpedo nAChR-enriched membranes was assayed as described under Experimental Methods. Various concentrations of rBgtx (squares, FIG. 5) or venom-derived (unlabeled) αBgtx (circles, FIG. 5) were incubated with 8 nM $^{125}$I-Bgtx and ~3 nM nAChR sites, as determined under saturation binding conditions, in microtiter plate wells for 2 hours. Unbound radioactivity was removed from the wells by washing, and the radioactivity remaining bound was determined. These values, expressed as a fraction of the counts bound in the absence of competitor, are plotted as a function of competitor concentration. Values are averages of duplicate determinations. The solid curves through the data points represent the best fits to the logistic equation as determined with Microcal Origin software.

Figure 5:
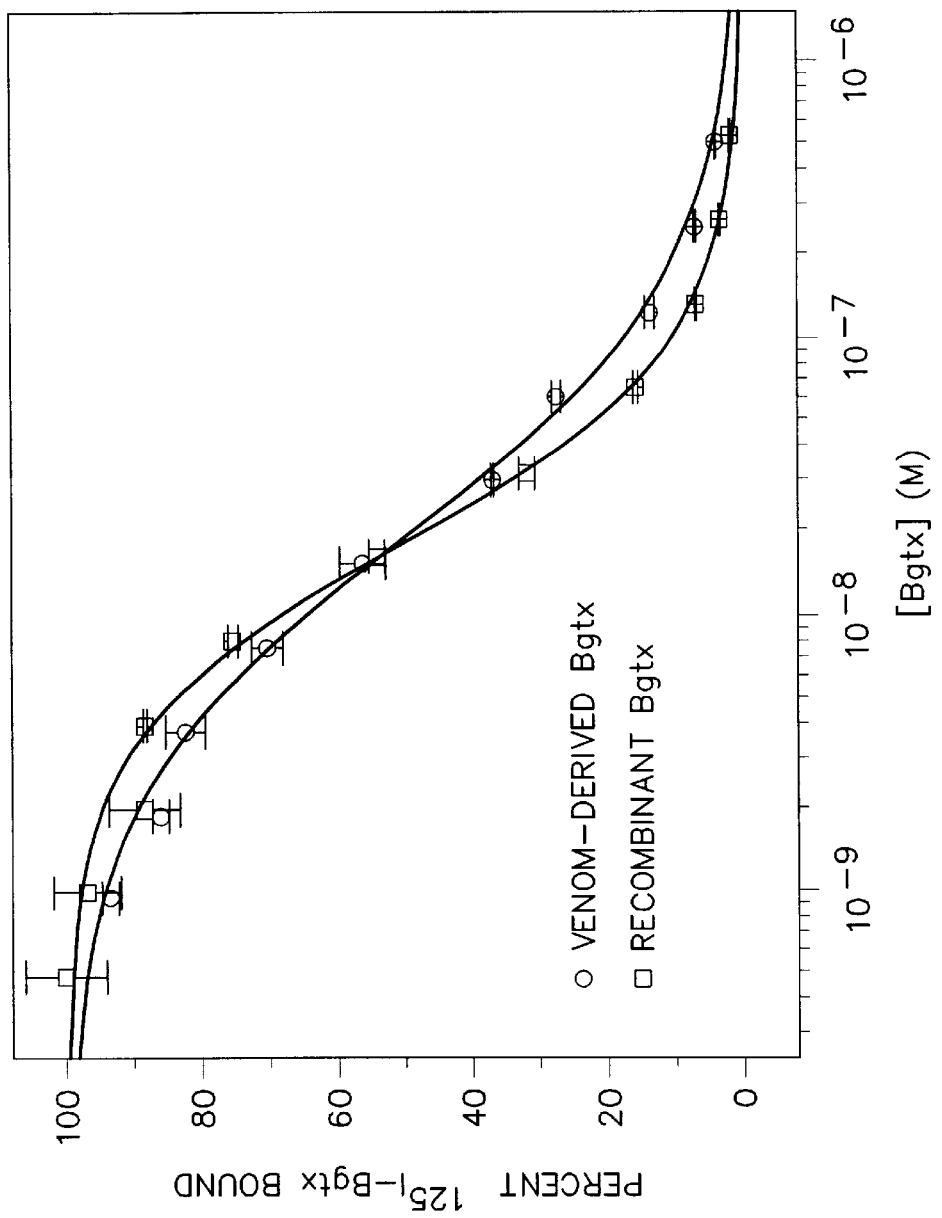
FIG. 5. Competition Binding Activity Analysis of rBgtx.
Figure 7A:
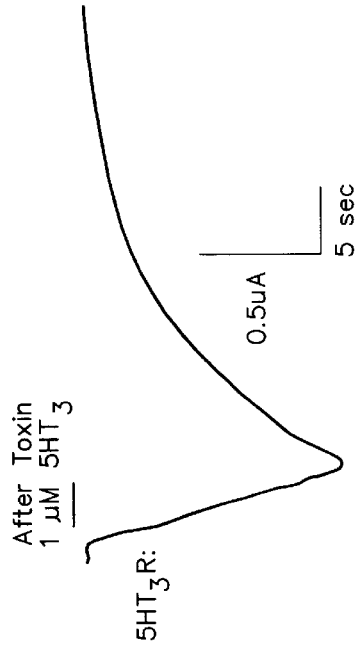
FIG. 7. A–D. Block of Macroscopic ACh-Evoked Currents by rBgtx-K38P/L42Q. E. Time Course of Recovery from Block by rBgtx-K38P/L42Q.
Figure 7B:
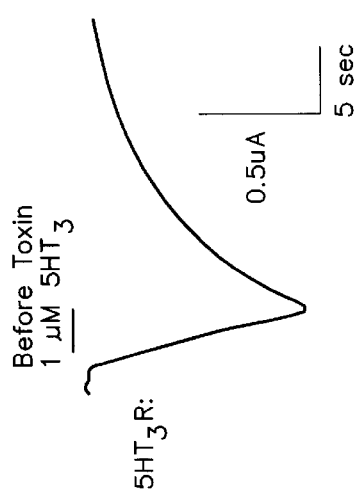
Figure 7C:
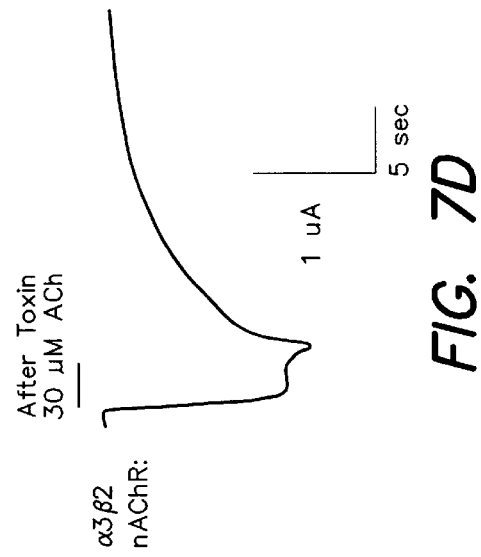
Figure 7D:
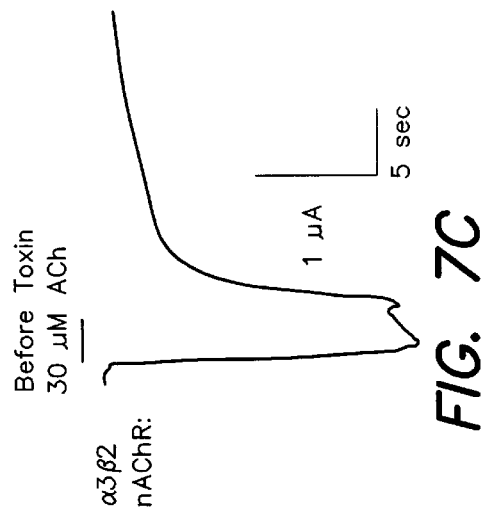
Figure 7E:
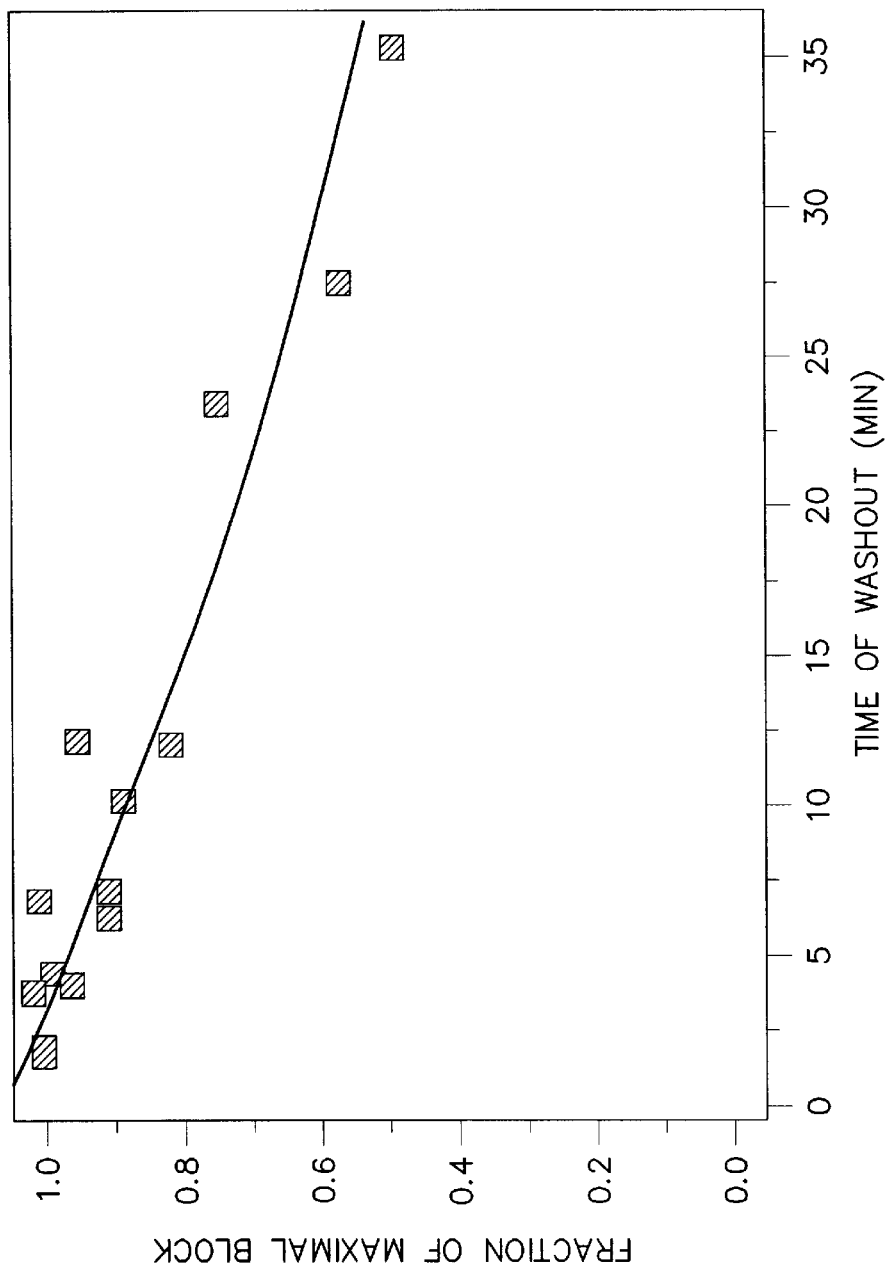

FIG. 5 shows a representative assay of the fully purified rBgtx and venom-derived αBgtx binding to Torpedo nAChR-enriched membranes, as measured by the competition of these unlabeled ligands with $^{125}$I-Bgtx. The competition curves are coincident, indicating identical binding affinity of the recombinant and venom-derived toxins. The Pichia-expressed recombinant αBgtx is also fully active in the blockade of acetylcholine-evoked currents from oocytes expressing either chick α7 or mouse muscle nAChRs (data not shown) as was found for E. coli-produced, N-terminal His-tagged rBgtx (Rosenthal, Ph.D. Thesis, Brown University, 1996; Rosenthal et al., 1999).

Figure 6:
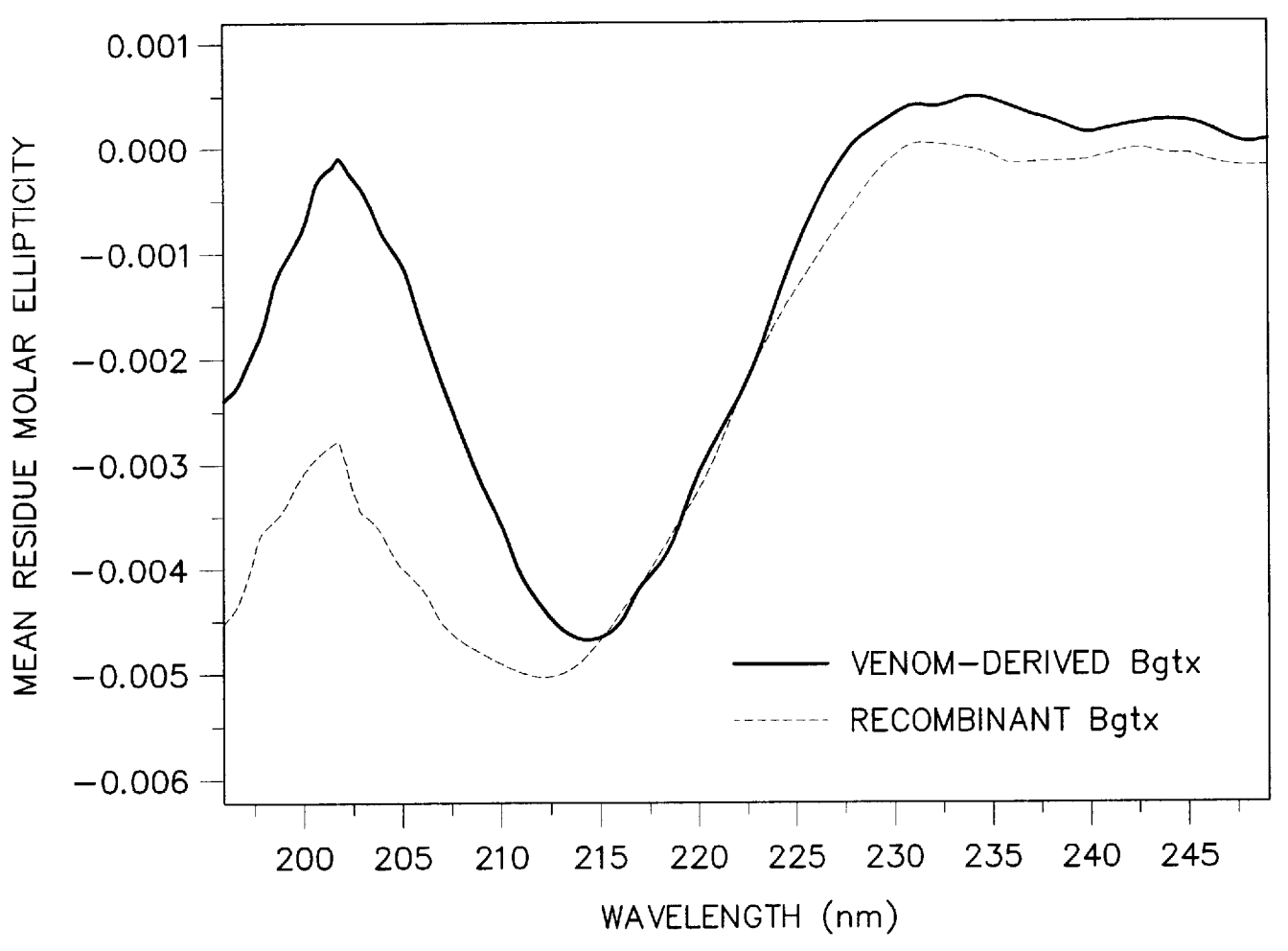

In addition, the circular dichroism spectra of the recombinant and authentic toxins were measured (FIG. 6). The circular dichroism spectra in the far UV range of venom-derived αBgtx (solid trace) recombinant Bgtx (dashed trace) were measured from 190–250 nm using a protein concentration of ~12 μM. The traces shown are the averages of three scans. Mean residue ellipticities were calculated taking into account the extra N-terminal five residues of the recombinant form of αBgtx. The overall similarity of the spectral profiles, taking into account the addition of five residues at the N-terminus of the rBgtx, indicates that the Pichia-secreted rBgtx has the same overall fold as the venom-derived αBgtx. The maxima at ~200 nm and the minima at ~215 nm are very indicative of considerable β-sheet structure (cf. Pillet et al., *J. Biol. Chem.* 68:909–916, 1993; Grant et al., 1998).

Mutants of Recombinant αBgtx. One of the major goals in expressing αBgtx recombinantly was to analyze the structure-function relationships of this classical nicotinic antagonist. Specifically, we wished to determine whether αBgtx could be engineered by site-directed mutagenesis so as to alter its nACh receptor binding selectively. In order to produce an αBgtx variant capable of recognizing neuronal nAChRs that are normally insensitive to wild type αBgtx, a double point mutant was prepared with Pro substituted for Lys38 and Gln substituted for Leu42. Pro and Gln residues in these positions are completely conserved in the κ-neurotoxin subfamily (Chiappinelli et al., 1996) and, in the stretch of amino acids 33–49, are the only significantly divergent residues between κ-neurotoxins and αBgtx. Importantly, κ-bungarotoxin blocks certain neuronal nACh receptors (Fiordalisi et al., *Biochem.* 33:3872–3877, 1994; Grant et al., 1998), and substitution of Lys for Pro at this position in κ-bungarotoxin significantly decreases its ability to block neuronal nAChRs (Fiordalisi et al., 1994).

Oocytes expressing rat α3β2 neuronal nAChRs were used to test the effect of the Lys38Pro/Leu42Gln mutation (rBgtx-K38P/L42Q). In this experiment, an oocyte expressing both the 5HT$_3$ receptor and the α3β2 neuronal nAChR was voltage clamped at a membrane potential of −60 mV. The two traces on the left show responses evoked by sequential 6-sec applications of 1 μM 5HT (top) and 30 μM ACh (bottom) with two minutes of control perfusion in between. The oocyte was then incubated for ten minutes in a sample of rBgtx-K38P/L42Q mutant toxin isolated by CM-Sephadex chromatography and dialyzed against oocyte perfusion buffer, OR2 (total protein concentration of 7.7 μM). Following this incubation, as indicated by the traces on the right, the same doses of 5HT (top) and ACh (bottom) were applied to the oocyte. The 5HT response is unaffected by incubation with the mutant toxin, whereas the ACh-evoked current was reduced by 37±4% (N=nine oocytes).

To determine the time course of recovery from block by rBgtx-K38P/L42Q, oocytes expressing α3β2 nAChRs were incubated for 30–45 minutes in a preparation of rBgtx-K38P/L42Q obtained from a Pichia culture that was induced using a different protocol from that used for the experiments of FIGS. 7A–D. The Pichia culture was grown in an enriched YPD medium prepared according to Invitrogen specifications prior to induction with methanol. Following induction, the cell-free culture supernatant was desalted, concentrated and then dialyzed against oocyte perfusion buffer, OR2. Oocyte incubation in this preparation (final protein concentration of ~2.5 μM) led to an 86±5% block of the pre-toxin response (N=four oocytes). This level of block is greater than that obtained in the studies described in FIGS. 7A–D (see above) and although the exact explanation for this presently unclear it is most probably related to fundamental variations, with different Pichia induction and growth conditions, in the levels of O-glycosylation of the mutant rBgtx. Following the initial incubation in rBgtx-K38P/L42, the ACh-evoked responses from these oocytes were measured at various times after washing out the toxin and continuously perfusing the oocytes. The fraction of initial maximal block is plotted as a function of the total time of perfusion in the absence of the toxin. The solid curve through the data is the best fit to a single exponential function and indicates that recovery from toxin block is characterized by a half-time of ~35 minutes. Four independent preparations of rBgtx-K38P/L42Q have shown significant blocking activity against α3β2 receptors.

FIG. 7 shows that ACh-evoked currents from oocytes expressing α3β2 receptors are inhibited by rBgtx-K38P/

L42Q. Venom-derived (wild type) αBgtx does not block α3β2 receptors, even at a concentration of 10 μM (Levandoski et al., 1999). A preparation of rBgtx-K38P/L42Q, partially purified through the same CM-Sephadex C-25 step used for purification of the wild-type rBgtx (e.g., FIG. 2), blocks α3β2-mediated currents, but does not block evoked currents from $5HT_3$ receptors co-expressed in the same cell (FIGS. 7A–D) arguing against a non-specific effect. The undiminished response to 5HT provides an internal control that the oocytes retain the capability of responding to another bath-applied agonist, and rules out non-specific toxic effects of the mutant rBgtx preparation which might otherwise appear as functional block. In other control experiments, Pichia medium alone, Pichia-expressed wild type αBgtx at comparable protein concentrations and comparable stages of purification, and an irrelevant Pichia-expressed $GABA_B$ receptor fragment (Hawrot et al., 1998) all fail to block of α3β2 nAChRs. In addition, as demonstrated in FIG. 7E, the notion that this blocking effect is due to some progressive, systematic decrease in the ACh response (often termed "run-down") can be ruled out because it was observed that oocytes recover from block following a continuous washout of the toxin. In these experiments, α3β2-expressing oocytes were incubated for 30–45 minutes in a preparation of rBgtx-K38P/L42Q that had been concentrated and dialyzed against oocyte recording buffer. The initial degree of block after incubation with mutant toxin was 86±5% in this experiment (N=4 oocytes). ACh-evoked responses were then measured at various times throughout the course of washing out the toxin, and the fraction of maximal block (compared to control responses measured prior to toxin exposure) was determined. This time course of recovery from block gives an indication of the rate of dissociation of the mutant rBgtx from the α3β2 nAChR, here characterized by a half-time of ~35 minutes.

As shown above, αBgtx can be used as a molecular scaffold for engineering new receptor specificities by site-directed mutagenesis. A mutant α-neurotoxin capable of recognizing α3β2 neuronal nAChRs was created by incorporating the two homologous residues of κ-bungarotoxin to create the double mutant rBgtx-K38P/L42Q. Partially purified samples from four different preparations of rBgtx-K38P/L42Q blocked ACh-evoked currents in oocytes mediated by α3β2 nAChRs (FIG. 7). For the experiments shown in FIG. 7A–D, the total protein concentration of the partially purified sample was approximately 7.7 μM. The 37% block of neuronal α3β2 nAChR obtained with this sample of rBgtx-K38P/L42Q would therefore be consistent with an apparent $IC_{50}$ of 13 μM assuming that the sample was homogenous which was not the case. The observed $IC_{50}$ value is therefore an upper limit and the affinity of the most active species in this preparation should be much greater than that reflected by the $IC_{50}$ obtained with the heterogeneous sample. In fact, the observed $t_{1/2}$ for recovery (~35 minutes) of α3β2 receptors blocked by rBgtx-K38P/L42Q is more consistent with an affinity in the nanomolar range (Levandoski et al., 1999).

The Pichia system for producing recombinant αBgtx is an improvement over its bacterial expression system predecessor (Rosenthal et al., *J. Biol. Chem.* 269:11178–11185, 1994; Rosenthal et al., *Biochem.* 38:7847–7855, 1999) because a recombinant αBgtx that has properties identical to venom-derived αBgtx can be obtained from *Pichia pastoris* without further refolding in vitro. Although there are many proteins that can be expressed at very high levels in Pichia (Higgins & Cregg, 1998), so far none of the attempts to increase the expression level of αBgtx in Pichia have been fruitful. The bacterially-produced fusion protein has a 250-fold lower apparent affinity than authentic rBgtx (Rosenthal et al., 1999), and the fully-active rBgtx is generated only after cleavage from the fusion partner and a laborious and inefficient refolding process. In contrast, high levels of toxin activity can be detected in the spent medium immediately following induction of Pichia cultures. Moreover, relatively crude preparations of an appropriately mutated αBgtx, requiring only dialysis against oocyte recording buffer, are active in blocking the acetylcholine-evoked responses of a neuronal nAChR. Thus, the Pichia system is amenable to rapid screening and identification of mutants of αBgtx for binding to neuronal nAChRs whereas the *E. coli* system is not.

Equivalents

Those skilled in the art will recognize, or be able to ascertain using no more than routine experimentation, many equivalents to the specific embodiments of the invention described herein. Equivalents include minor modifications to the domains described above whereby the modified domain retains the desired activity (or even has enhanced such activity), such as can be prepared and screened by conventional methodologies. Such equivalents are intended to be encompassed by the following claims.

All references disclosed herein are incorporated by reference in their entirety.

I claim:

1. A method of enhancing relaxation of muscle or slackening of cutaneous tissue, comprising: locally administering to a cutaneous tissue an isolated α-bungarotoxin molecule in an amount effective to enhance denervation of the muscle or group of muscles present subcutaneous to the cutaneous tissue to enhance relaxation of muscle or slackening of the cutaneous tissue.

2. The method of claim 1, wherein the α-bungarotoxin is administered subcutaneously.

3. The method of claim 1, wherein the relaxation or slackening of the cutaneous tissue results in lessening of wrinkles or fine lines of the skin.

4. The method of claim 3, further comprising co-administering an anti-wrinkle agent selected from the group consisting of hydroxy acids and retinoids.

5. The method of claim 4, wherein the hydroxy acid is selected from the group consisting of α-hydroxy acids and β-hydroxy acids, each selected from the group consisting of linear, branched, cyclic, saturated and unsaturated.

6. The method of claim 4, wherein the retinoid is selected from the group consisting of retinoic acid, retinol and retinol esters.

7. The method of claim 1, wherein the α-bungarotoxin molecule is an isolated α-bungarotoxin molecule or a fragment thereof that binds to a nicotinic aceyticholine receptor.

8. The method of claim 7, wherein the isolated a-bungarotoxin molecule comprises SEQ ID NO:2.

9. The method of claim 7, wherein the isolated α-bungarotoxin molecule comprises at least one amino acid substitution selected from the group consisting of a substitution at amino acid 38 and a substitution at amino acid 42 of SEQ ID NO:2.

10. A method of controlling autonomic nerve function in a subject, comprising: locally administering to a target tissue or organ of a subject in need of such treatment an isolated α-bungarotoxin, in an amount effective to enhance denervation in the target tissue or organ and control autonomic nerve function in the subject.

11. The method of claim 10, wherein the autonomic nerve function includes the function of an automatic nerve which contributes to at least one symptom or rhinorrhea, otitis media, excessive salivation, asthma, chronic obstructive pulmonary disease, excessive stomach acid secretion, spastic colitis or excessive sweating, 12. The method of claim 10, wherein the α-bungarotoxin molecule is an isolated α-bungarotoxin molecule or a fragment thereof that binds to a nicotinic aceytlcholine receptor.

13. The method of claim 12, wherein the isolated α-bungarotoxin molecule comprises SEQ ID NO:2.

14. The method of claim 12, wherein the isolated α-bungarotoxin molecule comprises at least one amino acid selected from the group consisting of a substitution at amino acid 38 and a substitution at amino acid 42 of SEQ ID NO:2.

* * * * *

UNITED STATES PATENT AND TRADEMARK OFFICE
CERTIFICATE OF CORRECTION

PATENT NO.    : 6,753,315 B2
DATED         : June 22, 2004
INVENTOR(S)   : Edward Hawrot It is certified that error appears in the above-identified patent and that said Letters Patent is hereby corrected as shown below:

<u>Column 25,</u>
Line 10, delete "aceyticholine" and replace with -- acetylcholine --.
Line 12, delete "a-bungarotoxin" and replace with -- α-bungarotoxin --

<u>Column 26,</u>
Line 5, delete "automatic" and replace with -- autonomic --
Line 6, delete "or" and replace with -- of --
Line 12, delete "aceytlcholine" and replace with -- acetylcholine --

Signed and Sealed this

Twenty-first Day of September, 2004

JON W. DUDAS
*Director of the United States Patent and Trademark Office*

SEQUENCE LISTING

<160> NUMBER OF SEQ ID NOS: 6

<210> SEQ ID NO 1
<211> LENGTH: 225
<212> TYPE: DNA
<213> ORGANISM: Bungarus multicinctus

<400> SEQUENCE: 1
attgtgtgtc atactactgc tacttctcct atttctgctg ttacttgtcc tcctggtgaa      60
aatttgtgtt acagaaaaat gtggtgtgat gcttttttgtt cttctagagg taaggtcgtt     120
gaattgggtt gtgctgctac ttgtccttct aaaaaaccttt acgaagaagt cacctgttgt     180
tctactgata aatgtaatcc tcatcctaaa caaagacctg gttaa                     225

```
<210> SEQ ID NO 2
<211> LENGTH: 74
<212> TYPE: PRT
<213> ORGANISM: Bungarus multicinctus

<400> SEQUENCE: 2

Ile Val Cys His Thr Thr Ala Thr Ser Pro Ile Ser Ala Val Thr Cys
1               5                   10                  15

Pro Pro Gly Glu Asn Leu Cys Tyr Arg Lys Met Trp Cys Asp Ala Phe
            20                  25                  30

Cys Ser Ser Arg Gly Lys Val Val Glu Leu Gly Cys Ala Ala Thr Cys
            35                  40                  45

Pro Ser Lys Lys Pro Tyr Glu Glu Val Thr Cys Cys Ser Thr Asp Lys
    50                  55                  60

Cys Asn Pro His Pro Lys Gln Arg Pro Gly
65                  70

<210> SEQ ID NO 3
<211> LENGTH: 5
<212> TYPE: PRT
<213> ORGANISM: Bungarus multicinctus

<400> SEQUENCE: 3

Tyr Ile Val Cys His
1               5

<210> SEQ ID NO 4
<211> LENGTH: 9
<212> TYPE: PRT
<213> ORGANISM: Bungarus multicinctus

<400> SEQUENCE: 4

Glu Ala Glu Ala Tyr Ile Val Cys His
1               5

<210> SEQ ID NO 5
<211> LENGTH: 4
<212> TYPE: PRT
<213> ORGANISM: Bungarus multicinctus

<400> SEQUENCE: 5

Glu Ala Glu Ala
1

<210> SEQ ID NO 6
<211> LENGTH: 5
<212> TYPE: PRT
<213> ORGANISM: Bungarus multicinctus

<400> SEQUENCE: 6

Glu Ala Glu Ala Tyr
1               5
```